(12) United States Patent
Howell et al.

(10) Patent No.: US 10,258,278 B2
(45) Date of Patent: *Apr. 16, 2019

(54) METHOD AND APPARATUS TO SENSE HYDRATION LEVEL OF A PERSON

(71) Applicant: IpVenture, Inc., Los Altos, CA (US)

(72) Inventors: Thomas A. Howell, Palo Alto, CA (US); Angeline Hadiwidjaja, Los Altos, CA (US); Peter P. Tong, Mountain View, CA (US); C. Douglass Thomas, Saratoga, CA (US); Corrine Schrall, Simi Valley, CA (US)

(73) Assignee: IpVenture, Inc., San Jose, CA (US)

( * ) Notice: Subject to any disclaimer, the term of this patent is extended or adjusted under 35 U.S.C. 154(b) by 216 days.

This patent is subject to a terminal disclaimer.

(21) Appl. No.: 15/231,292

(22) Filed: Aug. 8, 2016

(65) Prior Publication Data

US 2017/0027506 A1    Feb. 2, 2017

Related U.S. Application Data

(63) Continuation-in-part of application No. 14/279,483, filed on May 16, 2014, now abandoned, which is a
(Continued)

(51) Int. Cl.
*A61B 5/00* (2006.01)
*A61B 10/00* (2006.01)
(Continued)

(52) U.S. Cl.
CPC ........ *A61B 5/4875* (2013.01); *A61B 5/14507* (2013.01); *A61B 5/4277* (2013.01);
(Continued)

(58) Field of Classification Search
CPC .............. A61B 5/4875; A61B 10/0045; A61B 10/0051; A61B 5/6802; A61B 5/00;
(Continued)

(56) References Cited

U.S. PATENT DOCUMENTS 3,420,205 A     1/1969  Morison
4,126,132 A    11/1978  Portner et al.
(Continued)

FOREIGN PATENT DOCUMENTS

EP    0 274 363 B1    7/1988
EP    1 184 663 A3    3/2002
WO    2005/084531 A1  9/2005

OTHER PUBLICATIONS

"Comparison of a New Test for the Measurement of Resting Whole Saliva with the Draining and the Swab Techniques", Pia López-Jornet et al., Department of Oral Medicine, University of Murcia, Murcia, Spain, electronic publication: Feb. 1997, 6 pages.
(Continued)

*Primary Examiner* — Carl H Layno
*Assistant Examiner* — Jon Eric C Morales

(57) ABSTRACT

A hydration sensor or sensing element is configured to measure the hydration level of a user. The sensing element can include a water-permeable material positioned in between two water-impermeable materials. The sensing element can be coupled to a bottle of fluid, or a carrier with a timer. The sensing element can be incorporated into a handheld device. The sensing element can be a disposable element, an element applicable for more than one-time use, or a re-usable element. The sensing element or sensor can be calibrated for a specific user or a group of users. One or more additional sensors that do not measure hydration level of the user can be coupled to a hydration sensing element to determine the amount of fluid consumption for the user in different conditions.

15 Claims, 21 Drawing Sheets

Related U.S. Application Data continuation of application No. 11/592,431, filed on Nov. 2, 2006, now Pat. No. 8,734,341, which is a continuation-in-part of application No. 11/451,781, filed on Jun. 12, 2006, now abandoned, said application No. 11/592,431 is a continuation-in-part of application No. 11/314,545, filed on Dec. 20, 2005, now abandoned.

(60) Provisional application No. 62/256,901, filed on Nov. 18, 2015, provisional application No. 60/785,825, filed on Mar. 24, 2006, provisional application No. 60/732,925, filed on Nov. 2, 2005, provisional application No. 60/689,312, filed on Jun. 10, 2005, provisional application No. 60/670,957, filed on Apr. 13, 2005, provisional application No. 60/652,213, filed on Feb. 14, 2005, provisional application No. 60/636,969, filed on Dec. 20, 2004.

(51) Int. Cl.
  G01N 21/78 (2006.01)
  G01N 37/00 (2006.01)
  A61B 5/145 (2006.01)
  G01N 21/81 (2006.01)

(52) U.S. Cl.
  CPC ...... *A61B 10/0045* (2013.01); *A61B 10/0051* (2013.01); *G01N 21/81* (2013.01); *A61B 2560/0285* (2013.01); *A61B 2560/0431* (2013.01); *A61B 2562/0295* (2013.01); *Y10T 436/2575* (2015.01)

(58) Field of Classification Search
  CPC ............... A61B 5/4277; A61B 5/4869; A61B 2562/0295; A61B 5/14507; A61B 5/682; B01L 2300/0825; A61K 49/0004; G01N 21/78; G01N 37/005; Y10T 436/2575
  USPC .................................................. 600/300, 309
  See application file for complete search history.

(56) References Cited

U.S. PATENT DOCUMENTS

| | | | |
|---|---|---|---|
| 4,513,608 A | 4/1985 | Cuming | |
| 4,860,753 A | 8/1989 | Amerena | |
| 4,883,063 A | 11/1989 | Bernard et al. | |
| 5,014,798 A | 5/1991 | Glynn | |
| 5,231,993 A | 8/1993 | Haber et al. | |
| 5,353,802 A | 10/1994 | Ollmar | |
| 5,426,415 A | 6/1995 | Prachar et al. | |
| 5,495,961 A | 3/1996 | Maestre | |
| 5,563,584 A | 10/1996 | Rader et al. | |
| 5,580,794 A | 12/1996 | Allen | |
| 5,755,672 A | 5/1998 | Arai et al. | |
| 5,833,625 A | 11/1998 | Essen-Moller | |
| 5,843,691 A | 12/1998 | Douglas et al. | |
| 5,938,593 A | 8/1999 | Ouellette | |
| 6,107,537 A | 8/2000 | Elder et al. | |
| 6,248,067 B1 | 6/2001 | Causey, III et al. | |
| 6,319,199 B1 | 11/2001 | Sheehan et al. | |
| 6,370,426 B1 | 4/2002 | Campbell et al. | |
| 6,466,821 B1 | 10/2002 | Pianca et al. | |
| 6,485,982 B1 | 11/2002 | Charlton | |
| 6,523,392 B2 | 2/2003 | Porter et al. | |
| 6,529,446 B1 | 3/2003 | de la Huerga | |
| 6,529,767 B1 | 3/2003 | Woo et al. | |
| 6,569,094 B2 | 5/2003 | Suzuki et al. | |
| 6,602,469 B1 | 8/2003 | Maus et al. | |
| 6,623,698 B2 | 9/2003 | Kuo | |
| 6,766,817 B2 | 7/2004 | da Silva | |
| 6,780,307 B2 | 8/2004 | Kidwell | |
| 6,823,717 B2 | 11/2004 | Porter et al. | |
| 6,854,317 B2 | 2/2005 | Porter et al. | |
| 6,998,273 B1 | 2/2006 | Fleming et al. | |
| 7,170,823 B2 | 1/2007 | Fabricius et al. | |
| 7,273,454 B2 | 9/2007 | Raymond et al. | |
| 7,323,141 B2 | 1/2008 | Kirchhevel et al. | |
| 7,332,642 B2 | 2/2008 | Liu | |
| 8,734,341 B2* | 5/2014 | Howell ............... | A61B 5/4277 422/401 |
| 2002/0001852 A1 | 1/2002 | Mendel-Hartvig et al. | |
| 2002/0147617 A1 | 10/2002 | Schoenbaum et al. | |
| 2003/0002238 A1 | 1/2003 | Toyoda | |
| 2004/0121478 A1 | 6/2004 | Brinz et al. | |
| 2004/0133081 A1 | 7/2004 | Teller et al. | |
| 2005/0033200 A1 | 2/2005 | Soehren et al. | |
| 2005/0143675 A1 | 6/2005 | Neel et al. | |
| 2005/0169810 A1 | 8/2005 | Hagen et al. | |
| 2005/0228692 A1 | 10/2005 | Hodgdon | |
| 2006/0121548 A1 | 6/2006 | Robbins et al. | |
| 2006/0231109 A1 | 10/2006 | Howell et al. | |
| 2006/0241355 A1 | 10/2006 | Howell et al. | |
| 2006/0248946 A1 | 11/2006 | Howell et al. | |
| 2006/0278156 A1 | 12/2006 | Miller | |
| 2007/0024465 A1 | 2/2007 | Howell et al. | |
| 2007/0048224 A1 | 3/2007 | Howell et al. | |
| 2007/0213606 A1 | 9/2007 | Sherman et al. | |
| 2007/0225578 A1 | 9/2007 | Howell et al. | |
| 2007/0249059 A1 | 10/2007 | Stewart | |
| 2008/0025154 A1 | 1/2008 | MacDonald et al. | |
| 2008/0146890 A1 | 6/2008 | LeBoeuf et al. | |
| 2014/0249388 A1* | 9/2014 | Howell ............... | A61B 5/4277 600/309 |

OTHER PUBLICATIONS

"Hydration status measurement by radio frequency absorptiometry in young athletes, a new method and preliminary results," Daniel S. Moran et al., IoP electronic journals, Physiological Measurement, Feb. 2004, pp. 51-59.

"Sensing device that when implanted in the mouth can detect hydration levels in soldiers", News-Medical.net, Devices/Technology, May 18, 2004, 3 pages.

"Xerostomia Information for dentists, Helping patients with dry mouth", Bartels, Cathy L., http://www.oralcancerfoundation.org/dental/xerostomia.htm, downloaded Mar. 22, 2007, pp. 1-14.

"0136 A new method to measure viscosity in saliva", Becker, K., et al., http://iadr.confex.com/iadr/eur05/techprogram/abstract_67646.htm, downloaded Oct. 14, 2005, pp. 1.

BiODE, Technical White Paper #1, (undated) downloaded Dec. 6, 2006, pp. 1-2.

Brownlee, Christen, "Oral Exams, Saliva could provide an alternative for some diagnostic tests," www.sciencenews.org, vol. 168, Sep. 17, 2005, pp. 187-188.

Cambridge Viscometers: Accurate, Reliable and Proven Fluid Viscosity Measurement Technology, http://www.cambridgeviscosity.com/default.aspx, downloaded Dec. 6, 2006, p. 1.

Bossingham, et al. "Water balance, hydration status, and fat-free mass hydration in younger and older adults," Am. J. Clin. Nutr, 81, 2005, 1342-1350.

Casa, D.J. et al. "National Athletic Trainers' Association Position Statement: Fluid Replacement for Athletes," Journal of Athletic Training, 2003, vol. 35, No. 2, pp. 212-224.

Marketing Devices, http://www.courage-khazaka.de/products/marketing_products.htm, downloaded May 14, 2007, pp. 1-4.

Products for Dermatology, http://www.courage-khazaka.de/products/derma_products.htm, downloaded May 14, 2007, pp. 1-4.

Scientific Devices, http://www.courage-khazaka.de/products/scientific_rd_prod.htm, downloaded May 14, 2007, pp. 1-5.

E-pill Pill Bottle Multi Alarm, http://www.epill.com/bottle.html, downloaded Dec. 5, 2006.

Étude, "The Way to skin counseling," Operation Manual, 2005, front cover page and pp. 1-27.

GOJO Skin Care Lab, Fast, Effective Hand Cleaning, http://automotive.gojo.com/skin_care/, downloaded Nov. 29, 2006, pp. 1-2.

(56) References Cited

OTHER PUBLICATIONS

Helton, K.L. et al. "Interfacial instabilities affect microfluidic extraction of small molecules from non-Newtonian fluids," Lab Chip, 2007, 7, 1581-1588.
Kenney, et al. "Influence of age on thirst and fluid intake," Medicine & Science in Sports & Exercise, Official Journal of the American College of Sports Medicine, vol. 33, No. 9, 2001, 1524-1532.
"L'Oréal and STMicroelectronics applying semiconductors to skin aging," Press Release, Geneva, Oct. 18, 2002, pp. 2.
LifePoint Inc.—Saliva Based Testing Systems for the next generation, LifePoint® IMPACT® Test System, downloaded 2005, 2 pages.
Moritex USA Incorporated, Sensors & Meters, copyright 2004, http://www.moritexusa.com/products/product_category.php?plid=5&pcid=10, downloaded Apr. 19, 2006, pp. 1-2.
Mentes, Janet, PhD, APRN, BC, "Oral Hydration in Older Adults," AJN, vol. 106, No. 6, Jun. 2006, 40-49.
Murray, R. "Dehydration, Hyperthermia, and Athletes: Science and Practice," Journal of Athletic Training, vol. 31, No. 3, Sep. 1996, 248-249.
NELLCOR™ Oximax Sensors™, Tyco Healthcare Group, 2002, pp. 1-5.
Nellcor OxiMax, Sensor Selection Guide, Tyco Healthcare, Oct. 2002, 12 pages.
Principal of Operation (viscosity measurement), Norcross Corporation, http://www.viscosity.com/faq_poo.asp., downloaded Nov. 8, 2007, 1 page.
Cheuvront, S.N. et al "Hydration Assessment of Athletes," Sports Science Exchange 97, vol. 18, No. 2, 2005, p. 1-12.
Prince, R. "A disposable, self-administered Electrolyte Test," submitted to the Department of Electrical Engineering and Computer Science in partial fulfillment of the requirements for the degree of Master of Engineering in Electrical Engineering at the Massachusetts Institute of Technology, Feb. 2003, pp. 13-17.
Rener-Nantz J. in Current Protocols in Food Analytical Chemistry (2001) H1.3.1-H1.3.5, 2001 by John Wiley & Sons, Inc.
Sikdar, S. et al. In "Viscosity Measurements of Non-Newtonian Slurry Suspensions Using Rotating Viscometers," Ind. Eng. Chem. Process Des. Dev., vol. 18, No. 4, 1979, pg. 722-726.
Sorbero et al. Assessment of Pay-for-Performance Options for Medicare Physician Services: Final Report. RAND Health. May 2006.
Walsh, N.P. et al. "Saliva flow rate, total protein concentration and osmolality as potential markers of who body hydration status during progressive acut dehydration in humans," Archives of Oral Biology (2004) 49, 149-154.
Walsh, N.P. et al. "Saliva Parameters as Potential Indices of Hydration Status during Acute Dehydration," Med. Sci. Sports, Exerc., v. 36, No. 9, pp. 1535-1542, 2004.
First Office Action for CN Patent Application No. 200610150494.7.
Second Office Action for CN Patent Application No. 200610150494.7.
Third Office Action for CN Patent Application No. 200610150494.7.
Notice of Grant of Patent Right for CN Patent Application No. 200610150494.7, dated Jun. 30, 2011.
U.S. Appl. No. 11/314,545, filed Dec. 20, 2005.
U.S. Appl. No. 11/888,723, filed Sep. 2, 2007.
U.S. Appl. No. 11/821,150, filed Jun. 22, 2007.
Notice of Allowance for U.S. Appl. No. 11/592,431, dated Nov. 27, 2013.
Office Action for U.S. Appl. No. 11/592,431, dated Nov. 29, 2011.
Office Action for U.S. Appl. No. 11/592,431, dated Aug. 15, 2011.
Office Action for U.S. Appl. No. 11/592,431, dated May 13, 2011.
Office Action for U.S. Appl. No. 11/592,431, dated Dec. 3, 2010.
Restriction Requirement for U.S. Appl. No. 11/592,431, dated Oct. 19, 2010.

\* cited by examiner

METHOD AND APPARATUS TO SENSE HYDRATION LEVEL OF A PERSON

CROSS-REFERENCE TO RELATED APPLICATIONS

This application claims priority to U.S. Provisional Patent Application No. 62/256,901, filed Nov. 18, 2015, and entitled "METHOD AND APPARATUS TO SENSE HYDRATION LEVEL," which is hereby incorporated by reference.

This application is a continuation-in-part of U.S. patent application Ser. No. 14/279,483, filed May 16, 2014, and entitled "METHOD AND APPARATUS TO SENSE HYDRATION LEVEL OF A PERSON," which is hereby incorporated by reference, which application is a continuation of U.S. patent application Ser. No. 11/592,431, filed Nov. 2, 2006, now U.S. Pat. No. 8,734,341, and entitled "METHOD AND APPARATUS TO SENSE HYDRATION LEVEL OF A PERSON," which is hereby incorporated by reference, and which application is related to U.S. patent application Ser. No. 11/314,545, filed Dec. 20, 2005, and entitled "BOTTLE OF LOTION WITH A SENSOR," which is hereby incorporated herein by reference, which claims priority to each of: (i) U.S. Provisional Patent Application No. 60/636,969, filed Dec. 20, 2004, entitled "PREVENTIVE MEDICAL SYSTEMS, METHODS AND APPARATUS," and which is hereby incorporated herein by reference; (ii) U.S. Provisional Patent Application No. 60/652,213, filed Feb. 14, 2005, entitled "PREVENTIVE MEDICAL SYSTEMS, METHODS AND APPARATUS," and which is hereby incorporated herein by reference; (iii) U.S. Provisional Patent Application No. 60/670,957, filed Apr. 13, 2005, entitled "BOTTLE OF LOTION WITH A LOTION SENSOR," and which is hereby incorporated herein by reference; (iv) U.S. Provisional Patent Application No. 60/689,312, filed Jun. 10, 2005, entitled "PERSONAL AND PORTABLE BOTTLE," and which is hereby incorporated herein by reference; and (v) U.S. Provisional Patent Application No. 60/732,925, filed Nov. 2, 2005, entitled "METHOD AND APPARATUS TO SENSE HYDRATION LEVEL OF A PERSON," and which is hereby incorporated herein by reference.

This application also claims priority to: (i) U.S. Provisional Patent Application No. 60/689,312, filed Jun. 10, 2005, entitled "PERSONAL AND PORTABLE BOTTLE," and which is hereby incorporated herein by reference; (ii) U.S. Provisional Patent Application No. 60/732,925, filed Nov. 2, 2005, entitled "METHOD AND APPARATUS TO SENSE HYDRATION LEVEL OF A PERSON," and which is hereby incorporated herein by reference; and (iii) U.S. Provisional Patent Application No. 60/785,825, filed Mar. 24, 2006, entitled "MEDICAL MONITORING SYSTEM," and which is hereby incorporated herein by reference.

This application also claims priority to: (i) U.S. Provisional Patent Application No. 60/732,925, filed Nov. 2, 2005, entitled "METHOD AND APPARATUS TO SENSE HYDRATION LEVEL OF A PERSON," and which is hereby incorporated herein by reference; and (ii) U.S. Provisional Patent Application No. 60/785,825, filed Mar. 24, 2006, entitled "MEDICAL MONITORING SYSTEM," and which is hereby incorporated herein by reference.

In addition, this application is related to: (i) U.S. patent application Ser. No. 11/314,545, filed Dec. 20, 2005, entitled "BOTTLE OF LOTION WITH A SENSOR," and which is hereby incorporated herein by reference; (ii) U.S. patent application Ser. No. 11/451,781, filed Jun. 12, 2006, entitled "PERSONAL AND PORTABLE BOTTLE," and which is hereby incorporated herein by reference; (iii) U.S. patent application Ser. No. 11/451,780, filed Jun. 12, 2006, now U.S. Pat. No. 8,202,217, entitled "HEALTHCARE BASE," and which is hereby incorporated herein by reference; (iv) U.S. patent application Ser. No. 11/479,665, filed Jun. 30, 2006, now U.S. Pat. No. 8,118,740, entitled "MOISTURE SENSOR FOR SKIN," and which is hereby incorporated herein by reference; and (v) U.S. patent application Ser. No. 11/491,774, filed Jul. 22, 2006, entitled "PORTABLE CONTAINER WITH SPEAKER ATTACHED," and which is hereby incorporated herein by reference.

This application is also related to U.S. Provisional Patent Application No. 60/636,969, filed Dec. 20, 2004, entitled "PREVENTIVE MEDICAL SYSTEMS, METHODS AND APPARATUS," and which is hereby incorporated herein by reference.

This application is also related to U.S. Provisional Patent Application No. 60/652,213, filed Feb. 14, 2005, entitled "PREVENTIVE MEDICAL SYSTEMS, METHODS AND APPARATUS," and which is hereby incorporated herein by reference.

This application is related to U.S. Provisional Patent Application No. 60/670,957, filed Apr. 13, 2005 entitled, "BOTTLE OF LOTION WITH A LOTION SENSOR," and which is hereby incorporated herein by reference.

This application is related to U.S. Provisional Patent Application No. 60/689,312, filed Jun. 10, 2005 entitled, "PERSONAL AND PORTABLE BOTTLE," and which is hereby incorporated herein by reference.

BACKGROUND

In the United States alone, there are more than 30 million adult runners. To maintain proper body temperature, runners sweat. The water in the sweat needs to be replaced. Appropriate hydration is critical for runners, particularly those who are running for a long period of time. Improper hydration is one of the most common reasons why marathon runners require medical attention during races.

Dehydration causes numerous problems. Even being at one-percent dehydration can affect a runner's performance. For example, a one-percent dehydration may lead to a 10% decrease in performance, which can translate to about 1-hour delay over an extended race, such as a triathlon. In other words, a relatively small fluid loss, such as one pint, can decrease athletic performance by 10-15%. In addition to diminished performance, symptoms of dehydration include thirst, irritability, headache, weakness, dizziness, cramps, chills, vomiting, nausea, and head or neck heat sensations.

The severely dehydrated can go into shock and end up losing control of all of their bodily functions. Though terribly thirsty, they cannot drink. Even ice chips in their mouths might make them vomit. At that point, to replenish the lost fluids, they need to have fluids applied intravenously.

Dehydration is not the only problem. Over-hydration can be problematic as well. Runners lose not only water, but also a certain amount of sodium and other minerals while sweating. Runners can consume large quantities of water during their races. This can cause a drop in overall sodium levels and, potentially, hyponatremia, which means low levels of salt in the blood. The problem typically arises when the runner runs for a long duration of time, such as three hours, while drinking only plain water.

The human body plays a delicate balancing act with the concentration of sodium in the blood. Small changes in the balance can be dangerous to a body's osmotic chemistry. Almost every physiological process in our body depends on osmotic gradients, with water moving from an area of lower salt concentration to an area of higher salt concentration. Severe sodium imbalance may lead to seizures, increased intracranial pressure, pulmonary edema (fluid in the lungs), respiratory arrest and even death. Many scientists view hyponatremia being as threatening to runners as dehydration and heat sickness.

To prevent dehydration or over-hydration, one approach is to drink the amount of fluid substantially equal to the sweat and urine losses.

Sometimes thirst may be a good indicator as to when to drink. If you are thirsty, drink. Monitoring the volume and color of urine can be helpful in determining hydration status as well. A general guideline is to drink until your urine is clear. However, by the time you feel thirsty, for example during a workout, you may already be dehydrated. Also, in the heat of a race, a runner may forget or suppress the natural instinct of thirst and not check his urine.

Another approach to determine when to drink is to measure one's body temperature. One recent approach is to swallow a small temperature sensor. However, some athletes may not want to swallow such a foreign object.

One recommendation from a number of marathon associations is to weigh runners prior to a race and again following the race. The drop in weight post-exercise could provide an indication as to roughly how much fluid one needs to replenish. In the heat of a long race, it may not be convenient to weigh oneself during the race. Also, runners must exercise care when stopping to weigh themselves in the middle of a race. Postural hypotension is experienced when a runner suddenly stops. Blood pooling in the legs can lead to inadequate blood supply to other parts of the body. The runner can then feel faint and collapse.

Although running has been used above as an example to illustrate the importance of proper hydration, proper hydration is important in other types of sports, particularly for endurance sports or sports lasting for a long duration of time. The challenges not only fall on the adults, but children as well.

Hydration is also an issue in children. It can be quite difficult to determine whether a toddler is sufficiently hydrated. We cannot depend on whether he is crying or not. He can be distressed for numerous reasons, and the basic reason may not be easily decipherable. The difficulty is exacerbated if the toddler has diarrhea and is vomiting. Typically, particularly for first-time parents, they often take the toddler to a healthcare provider.

It should be apparent from the foregoing that there is a need for ways to determine if a person is appropriately hydrated. Furthermore, it is desirable that the ways be applicable to people of different ages and in different conditions. Also, it would be helpful if at least some of the ways are affordable so that people with limited means can still use them.

SUMMARY

In different embodiments, the present invention provides methods and apparatus to measure the hydration level of a user based on measuring the saliva of the user. The measurements can be used to indicate if the user is appropriately hydrated. Different embodiments are applicable to people of different ages and in different conditions. Some embodiments are inexpensive and disposable. Other embodiments are applicable for more than one-time use. Yet other embodiments are applicable for continual use or re-use.

The invention can be implemented in numerous ways including, a method, system, device, and a computer readable medium. Several embodiments of the invention are discussed below.

In one embodiment, a hydration sensor includes a hydration sensing element. The sensing element can be a disposable sensing element. The sensing element includes a piece of water-permeable material, such as a blotting paper, which can be a piece of filter paper. The blotting paper is sandwiched between two pieces of water-impermeable material. In one example, the water-impermeable materials can be adhesive tapes. To measure the hydration level of a user, the sandwiched blotting paper is placed in the user's mouth. Based on capillary action, saliva gets into the paper from the edges. In one embodiment, the rate at which the saliva flows into the paper is a function of the concentration of water in the saliva, or depends on the viscosity of the saliva. By measuring the extent to which the saliva gets into the paper, the hydration level of the user can be determined.

In one embodiment, the sandwiched blotting paper includes a chemical compound deposited on a first side of the blotting paper. The second side of the paper is exposed to saliva, which diffuses or wicks into the first side. The compound when exposed to saliva or water becomes a conspicuous colored patch. This color patch diffuses back to the second side of the blotting paper. The amount or the extent of the compound that changes color depends on how dehydrated the user is and the duration the paper is in the mouth. For example, if the duration of time is fixed, the amount of the compound that changes color provides an indication on the hydration level of the user.

In one embodiment, the hydration sensing element is a hydration sensor. In another embodiment, the hydration sensing element is incorporated into different apparatus to form a hydration sensor. For example, the element is incorporated to a bottle, which can carry fluid. In another embodiment, the element is incorporated to a carrier, such as a box, which can include a clip to attach the box to the clothing of the user. The box can have a timer. The user can turn on the timer after placing the element into his mouth. After a preset amount of time, the timer will alert the user that the measurement is over and the user can remove the element from his mouth to check for his hydration level. In yet another embodiment, the sensor is a handheld device, which can carry a number of sensing elements.

In one embodiment, a hydration sensor incorporates electrical components to automatically measure a hydration sensing element, such as measure visual indications on the element. For example, the hydration sensor includes photodiodes and photo-sensors to measure the element.

Instead of based on visual indications, in one embodiment, sensing is performed through other electrical means. There can be electrically conducting lines on a piece of water-permeable material, such as blotting paper. The sensor measures the time it takes saliva to diffuse from one electrical line to the next to indicate the hydration level of the user. Instead of on a piece of paper, the conducting lines may be attached to a piece of cloth or a piece of fiberglass cloth. In one embodiment, such sensors are applicable for more than one-time use.

In one embodiment, a hydration sensing element is reusable, or more adaptable to be used numerous times. For example, the sensing element can include a hollow tube or chamber with a small diameter, with conducting wires inside the tube or chamber. The ends of the wires are staggered relative to the opening of the tube. A timer is used to measure the time it takes for saliva to go from one wire end to another wire end. Based on the time measured, the hydration level of the person can be identified. To re-start measurements, saliva in the tube is cleared. There can be different ways to clear the saliva from the tube. One approach is based on a mechanical air pump.

In another embodiment, a re-usable hydration sensor with a mechanical pump can be made in the shape to fit into the mouth of the user. The mechanical pump is activated by the user biting onto the sensor. The sensor includes a wireless transmitter to send measurements to, for example, a portable device. Based on the measurements received, the portable device can alert the user if he needs to drink.

Instead of a mechanical pump, in one embodiment, the saliva is cleared from the tube with an electro-mechanical pump.

The sensing elements can be made of other types of materials. In one embodiment, the sensing element is a piezoelectric element on an absorbent medium, such as a thin sponge, to measure the viscosity of fluid. The sensor can be used to provide an absolute index of the hydration level of a user.

Different people in different physical and/or environmental condition may need differing amounts of fluid. In one embodiment, a hydration sensor is calibrated. The calibration can be for different types of people in different conditions. A user can perform the calibration. After the calibration, the sensor or that type of sensor can become personalized to the user. For example, before a person starts using a hydration sensor or a type of hydration sensor, the person first gets herself appropriately hydrated. Then, she measures the time it takes for the sensor to indicate that she is appropriately hydrated. The time measured would serve as the base line. Future measurements can be relative to the base line.

An embodiment of a sensor with a wireless transmitter has been described. In one embodiment, the sensor is connected to another device through the wireless transceiver. The connection allows the measured hydration levels to be transmitted to the other device, and allows the sensor to receive signals from the other device, such as recommendation on fluid consumption. The other device can be a portable device also carried by the user, a device not in the vicinity of the user, or a base station in the vicinity of the user. In another embodiment, the sensor is connected to another device through a cable.

Different embodiments regarding packaging the sensor have been described. In other embodiments, the sensor can be incorporated into a spoon or a cup. In another embodiment, a hydration sensor is integrated to a bottle or a container, which can carry fluid or beverages for the user to drink. Some of the electronics in the sensor can be transferred to the bottle or the container. There can be promotional materials or different designs on one or more surfaces of the bottle or the container.

In one embodiment, one or more additional sensors are integrated or coupled to a hydration sensor. The one or more additional sensors are for sensing, for example, a piece of environmental information in the immediate vicinity of the hydration sensor. The additional sensor can be a temperature sensor or a humidity sensor. In another embodiment, an additional sensor can measure another piece of information regarding the person using the hydration sensor, such as the person's body temperature or activity level. The additional sensor information can help determine the appropriate amount of fluid for the user to consume. In another embodiment, the additional sensor information can modify the baseline calibration level of the sensor.

In one embodiment, a hydration sensor also provides recommendation to a person using it. The recommendation can be alerting the person to be aware of other factors that can affect the measurements. For example, an audio signal can tell the person to avoid eating food such as candy immediately before measurements.

Other aspects and advantages of the present invention will become apparent from the following detailed description, which, when taken in conjunction with the accompanying drawings, illustrates by way of example the principles of the invention.

Same numerals in FIGS. 1-15 are assigned to similar elements in all the figures. Embodiments of the invention are discussed below with reference to FIGS. 1-15. However, those skilled in the art will readily appreciate that the detailed description given herein with respect to these figures is for explanatory purposes as the invention extends beyond these limited embodiments.

DETAILED DESCRIPTION

In one embodiment, a hydration sensing element measures the hydration level of a user based on measuring the saliva of the user. The sensing element can be configured to measure the viscosity of the saliva of the user. Typically, when the user is well hydrated, his saliva has a higher concentration of water or is less viscous than when he is dehydrated. If the saliva is less viscous, it would wick or move faster or deeper by capillary action into the sensing element. FIGS. 1A-1G illustrate different embodiments of a hydration sensing element more applicable for one-time use.

Figure 1A:
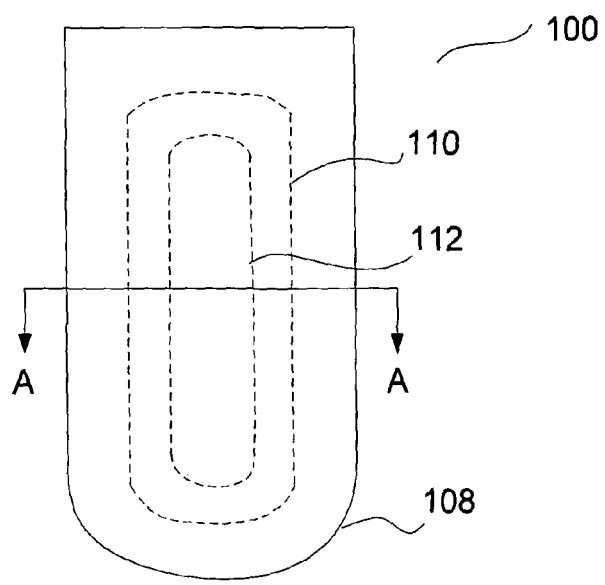
FIGS. 1A-1G illustrate different embodiments of disposable hydration sensing elements according to the invention.
Figure 1B:
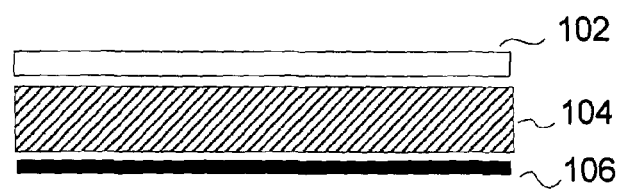

FIG. 1A shows the top view and FIG. 1B shows a cross-sectional view at AA of one embodiment of a hydration sensing element 100. The element 100 can be a disposable hydration sensor, designed to be used once and then disposed. The element 100 includes a piece of water-permeable material 104, such as blotting paper, sandwiched between two pieces of material, 102 and 106, that are impermeable or substantially impermeable to water. In one embodiment, the water-impermeable material can be adhesive tape. To measure the hydration level of a user, at least a portion of the element 100 is placed in the user's mouth. From at least one of its edges, such as 108, and based on capillary action, saliva diffuses or wicks into the water-permeable material 104. The dryness of the user's mouth, or the characteristics of the user's saliva, determines the amount of saliva getting into, or how far or deep the saliva seeps into, the water-permeable material 104. For example, there can be a number of rings on the paper, such as 110. The user can be considered as well hydrated if within one minute, saliva reaches the inner ring 112 on the paper 104.

In one embodiment, the water-permeable material 104 can be a piece of white filter paper, such as similar to the paper used for coffee filters. In one example, the water-permeable material 104 can be about 4 mils thick. In another example, the water-permeable material 104 can be sandwiched between a piece of translucent (or transparent) tape 102 and a black tape 106. The area where the water-permeable material 104 is wet becomes translucent, allowing the black tape 106 to be seen through the tape 102. As an example, for a normal person, after one minute in his mouth, saliva might extend into the water-permeable material 104 a distance of about 2 millimeters when he is appropriately hydrated. But if the person is dehydrated, saliva might extend in by less than 0.5 millimeter, again after the sensing element is in his mouth for 1 minute.

Instead of seeping in from the edge, in another embodiment, saliva can seep into a sensing element through an opening or hole not at the edge. To illustrate, again the water-permeable material 104 can be sandwiched between two pieces of tape. The edges of the sandwiched water-permeable material 104 are sealed to prevent saliva from getting in. However, there is a hole or an opening in the middle of one of the tapes. The time it takes for the saliva to extend outward from the middle of the opening can be used to determine the dryness of the mouth.

Figure 1C:
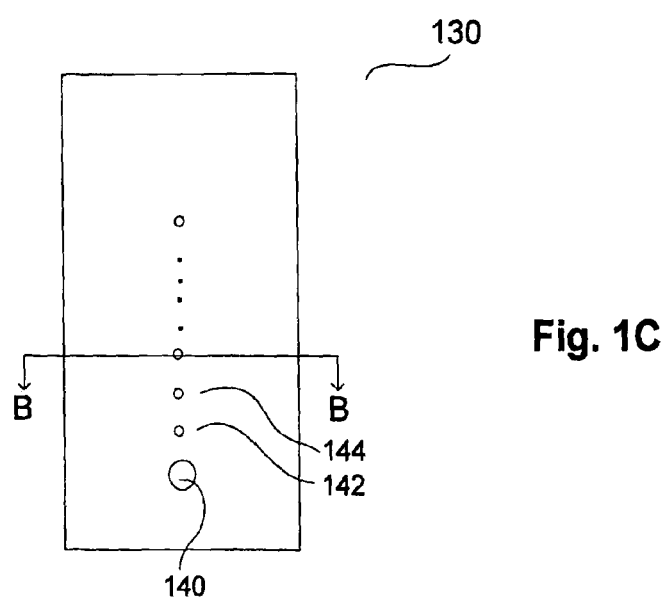
Figure 1D:
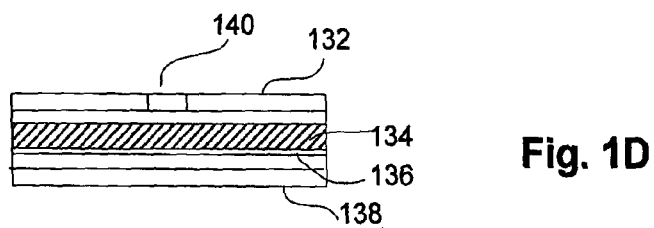

FIG. 1C shows a top view and FIG. 1D shows a cross-sectional view at BB of another embodiment of a hydration sensing element 130. The hydration sensing element 130 includes a water-permeable material 134 sandwiched between two water-impermeable materials 132 and 138. The element 130 can be a disposable hydration sensing element.

In one embodiment, the water-permeable material 134 can be a piece of blotting paper, which again can be a white filter paper. The water-permeable material 134 includes a chemical compound 136 on or coupled to one side, the first side, of the water-permeable material 134. For example, the chemical compound 136 is deposited on the first side (or a portion of the first side). The two water-impermeable materials again can, for example, be tape. A piece of tape (the first-side tape) 138 covers the compound 136. The second side of the water-permeable material 134 is also covered by tape (the second-side tape) 132. In one embodiment, both tapes are not transparent, and can be opaque. The edges of the tapes 132 and 138 are sealed to each other. The second-side tape 132 has an opening 140 that exposes the water-permeable material 134 to saliva. The second-side tape 132 is mostly opaque except having a number of transparent holes 142 and 144 (or spots or circles) at varying distances from the opening. The transparent holes 142 and 144 provide windows to visually see the water-permeable material 134 from the outside. In one embodiment, such as shown in FIG. 1C, the transparent holes 142 and 144 can be arranged in a line from the opening 140.

In one embodiment, when liquid, such as saliva, touches the water-permeable material 134, the saliva diffuses or wicks through it to the chemical compound 136 underneath. The part of the chemical compound 136 that gets wet becomes a conspicuous and/or visible color patch, and the visible patch diffuses or wicks through to the second side of the water-permeable material 134. For example, a colored (e.g., green) patch can appear on the second side. In one implementation, the chemical compound 136 is a water-based paint that is non-toxic and hypoallergenic. When saliva is mixed with the paint, the paint diffuses from the first side to the second side of the water-permeable material 134. In another example, the chemical compound 136 is a dye, such as a powdered food dye. Again when saliva reaches the dye, the dye diffuses from the first side and shows up on the second side of the paper.

When the sensing element 130 is in the mouth of the user, saliva gets into the opening 140, goes through the water-permeable material 134 (e.g., white filter paper) and reaches the chemical compound 136. The chemical compound 136 that is exposed to saliva generates a patch of color, such as a green color on the white filter paper. The green color extends back to the second side of the water-permeable material 134, or the side with the opening. The number of spots changing color from, such as, white (the color of the paper) to green (the color of the patch) depends on the duration the element 130 is within the mouth and the hydration level of the user. In one embodiment, if one fixes the time the element 130 is to stay in the user's mouth, based on the number of spots that have changed color, the hydration level of the user can be inferred. In another embodiment, the transparent spots are in the shape of alphanumeric symbols, such as numbers. For example, a transparent number closest to the opening 140 can be a numeral one, the second most closest transparent number can be a numeral two and so on. In other words, for numbers, the numbers can be in a sequence, such as in ascending order, or in descending order.

As described above, in one embodiment, a hydration sensing element includes a piece of water-permeable material with a first side and a second side, a chemical compound coupled to the first side of the water-permeable material, and a first piece and a second piece of water-impermeable material. The chemical compound is located between the first piece of water-impermeable material and the first side of the water-permeable material, while the second piece of water-impermeable material is coupled to the second side of the piece of water-permeable material. In other words, the water-permeable material is located between the two pieces of water-impermeable material. When the hydration sensing element is placed in the mouth of the user, saliva is allowed to reach the water-permeable material and the chemical compound. When saliva is in contact with the chemical compound, the part of the chemical compound that gets wet becomes a visible color patch. At least a portion of one piece of the water-impermeable material is transparent to show at least a portion of the visible color patch. The hydration level of the person is measured depending on the extent of the color patch.

There are different embodiments related to the chemical compound, the water-permeable material and the two pieces of water-impermeable material. These embodiments can be mixed and matched.

One embodiment relates to how saliva reaches the water-permeable material and the compound. In one configuration, at least one edge of the water-permeable material is exposed to allow the saliva to reach the water-permeable material and the compound. In another configuration, there is an opening on either the first or the second piece of water-impermeable material to allow saliva to reach the water-permeable material and the compound.

One embodiment relates to the transparency or the lack of transparency of the two pieces of water-impermeable material. Note that the two pieces can be made of different types of material. In one configuration, one piece of water-impermeable material is transparent. In another configuration, one piece of water-impermeable material is transparent, and the other piece of water-impermeable material is either opaque or translucent. In yet another configuration, the at least a portion of one piece of water-impermeable material that is transparent is in the shape of an alphanumeric symbol.

One embodiment relates to the physical structure or the shape of the chemical compound. In one configuration, the chemical compound is in the shape of a layer or a sheet. The sheet is coupled to the first side of the water-permeable material. In another configuration, the compound is in the form of particles. A number of such particles are at different positions on the first side of the water-permeable material. For example, the compound is a powdered or granular dye. The compound can be food dye, and can be in tiny concentrated grains. With sufficient water, liquid or saliva, the powdered or granular dye can create a conspicuous color patch across at least a portion, which can be a significant portion, of the water-permeable material. In one embodiment the grains deposited at different locations are not of the same color, such as two different colors at two different locations on the water-permeable material.

One embodiment relates to where a color patch is seen. In one configuration, the water-impermeable material with at least a portion being transparent is the second piece of water-impermeable material. At least a portion of a color patch permeates from the first side to the second side of the water-permeable material to be seen through the second piece of water-impermeable material. In another configuration, the water-impermeable material with at least a portion being transparent is the first piece of water-impermeable material.

In one embodiment, a hydration sensing element is a hydration sensor. In another embodiment, a hydration sensing element is incorporated into different apparatus to form a hydration sensor. For example, a hydration sensing element, such as one shown in FIGS. 1C-1D, can be attached to the end of a small rod or a handle. The hydration sensing element with the handle can become a hydration sensor.

In one embodiment, a hydration sensor includes at least three pieces of material on a substrate. The substrate can be a rigid structure, such as a handle or a stick (e.g. wooden stick or plastic stick). The three pieces of material are, for example, a piece of water-permeable material sandwiched between two pieces of water-impermeable or substantially water-impermeable material. There can be chemical compound on the water-permeable material. The sensor includes at least one aperture to allow saliva to reach the water-permeable material, and to the chemical compound via the water-permeable material. The chemical compound can change when the compound gets wet, such as changing its visual appearance. The change can be observable, such as through one of the pieces of water-impermeable material. Also, the sensor can include an indicator to provide an indication on the hydration level of a user. As an example, the indicator includes a number of reference marks.

The piece of water-permeable material can be a piece of absorbent material, such as absorbent paper. In one example, the piece of absorbent paper is a piece of paper towel. The two pieces of at least substantially water-impermeable material can be thin plastic sheets or films, such as about 1.5 mil thick. At least one piece of the water-impermeable material can be substantially transparent. The three pieces of materials can be laminated together.

The chemical compound on the water-permeable material can vary depending on different implementations. In one example, the chemical compound is dry powered food color. In another example, the compound can be non-toxic water soluble ink. In one embodiment, when the compound gets wet, the compound changes its visual appearance, such as by smearing or spreading across the water-permeable materials in an observable manner.

In one embodiment, the aperture can be formed by cutting the three pieces of materials after they are laminated. The edge of the cut can provide the aperture.

The indicator could provide an indication of the hydration level of a user, based on, for example, time measurement regarding the change of the compound, or the change of at least a portion of the water-permeable material, after the sensor is placed in contact with the saliva of the user. In one embodiment, the indicator includes a number of lines, each made with the compound. The compound can be water-soluble ink, with the indicator printed on the water-permeable material via an inkjet printer. As saliva gets into the sensor via the aperture, the line that the saliva touches smears. The hydration level of the user depends on the number of lines smeared by the saliva. In one example, the indicator can include numbers next to the lines. In one approach, the numbers are not made of the compound and do not smear when saliva touches them.

In one embodiment, one machine is responsible for both the cutting of the three pieces of the materials to create the aperture, and the printing of the indicator. The position of the aperture relative to the indicator can be easier to control if done by one machine.

In one embodiment, the substrate can be a popsicle stick or a tongue depressor.

In one approach, to apply the sensor, a user presses the sensor onto her tongue with the aperture touching the tongue. After a preset amount of time, such as twenty or thirty seconds, the user removes the sensor from the tongue, and looks at the number of lines smeared by the user's saliva. The number of lines provides an indication on the hydration level of the user.

In one embodiment, the substrate can be a piece of plastic, such as PET or styrene, which can be ⅛ of an inch thick. One approach to attach the different pieces together is to use hot-melt glue. A piece of water-impermeable material can be a thin piece of substantially-transparent plastic pre-coasted with hot-melt glue on one side. One way to make the sensor is to put chemical compound (with the indicator, if preferred) on the water-permeable material. Then place the water-permeable material in between two piece of water-impermeable material, both with their hot-melt glue facing the water-permeable material. After that, a heated roller can go over the three pieces of the material to laminate or sandwich them together. Then the laminated pieces of material are glued or taped onto the substrate. After that, one edge of the substrate or the handle with the laminated pieces can be cut to create an aperture.

Figure 1E:
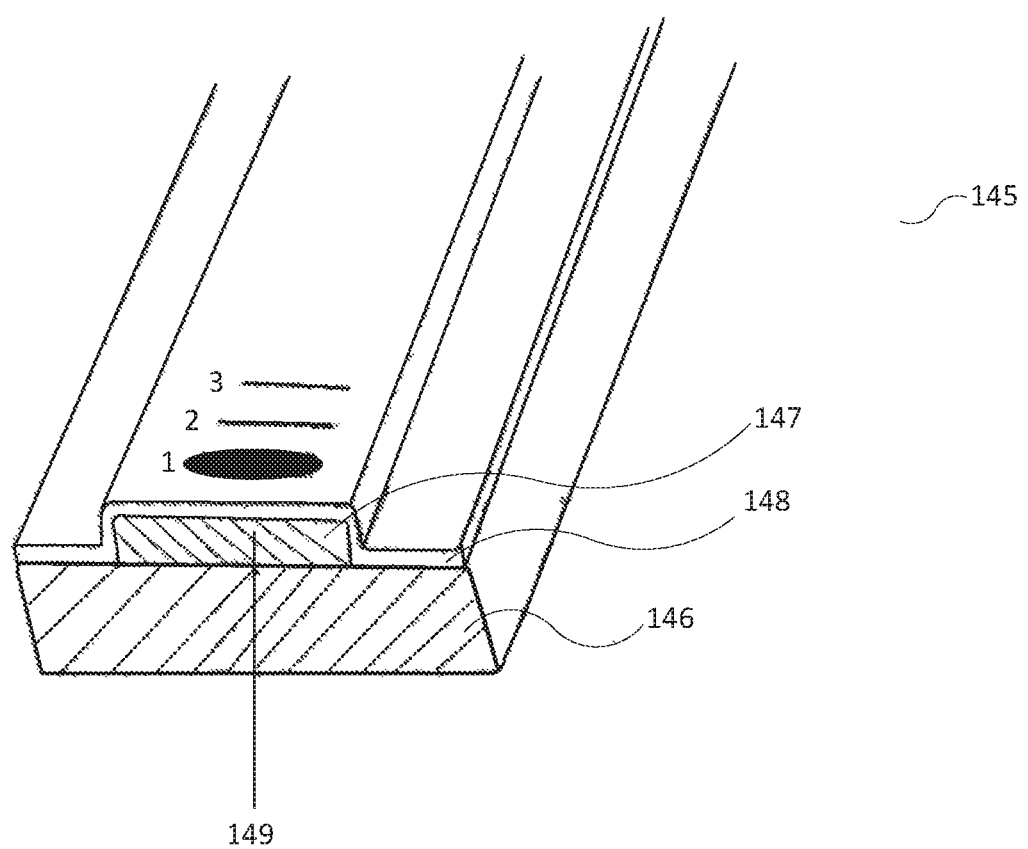

FIG. 1E shows another embodiment of a sensor 145 with the substrate serving as one piece of the water-impermeable material. One way to make the sensor 145 is to have hot-melt glue on top of the substrate 146 (such as a piece of plastic) of the sensor. Chemical compound (with the indicator, if preferred) can be put on one side of a piece of water-permeable material 147. The side without the compound can be placed on top of the substrate 146, facing the hot-melt glue. On top of the piece of water-permeable material 147 can be a piece of water-impermeable material 148, which can be substantially transparent. This piece of water-impermeable material 148 can include hot-melt glue on its bottom facing the water-permeable material. After that, the piece of water-impermeable material 148, the piece of water-permeable material 147, and the substrate 146 can be laminated together. After the lamination, one edge can be cut to create an aperture 149. In another approach, instead of having hot-melt glue on top of the substrate 146, hot-melt glue is put on the piece of water-permeable material 147; the hot-melt glue could be on the side of the water-permeable material opposite to the chemical compound.

In one embodiment, an indicator is not put on the water-impermeable material. Instead, the indicator or at least a part of the indicator can be on top of the piece of water-impermeable material 148, or on an outside surface of the sensor. In this embodiment, the compound can still be on the water-permeable material.

Figure 1F:
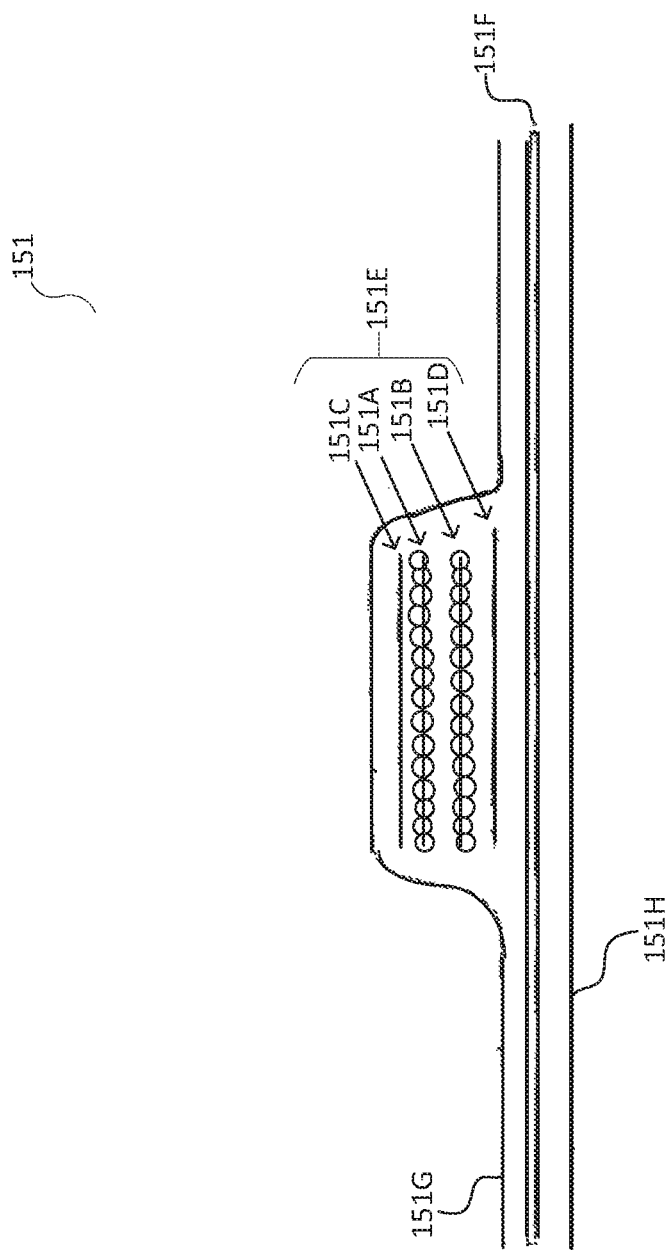
Figure 1G:
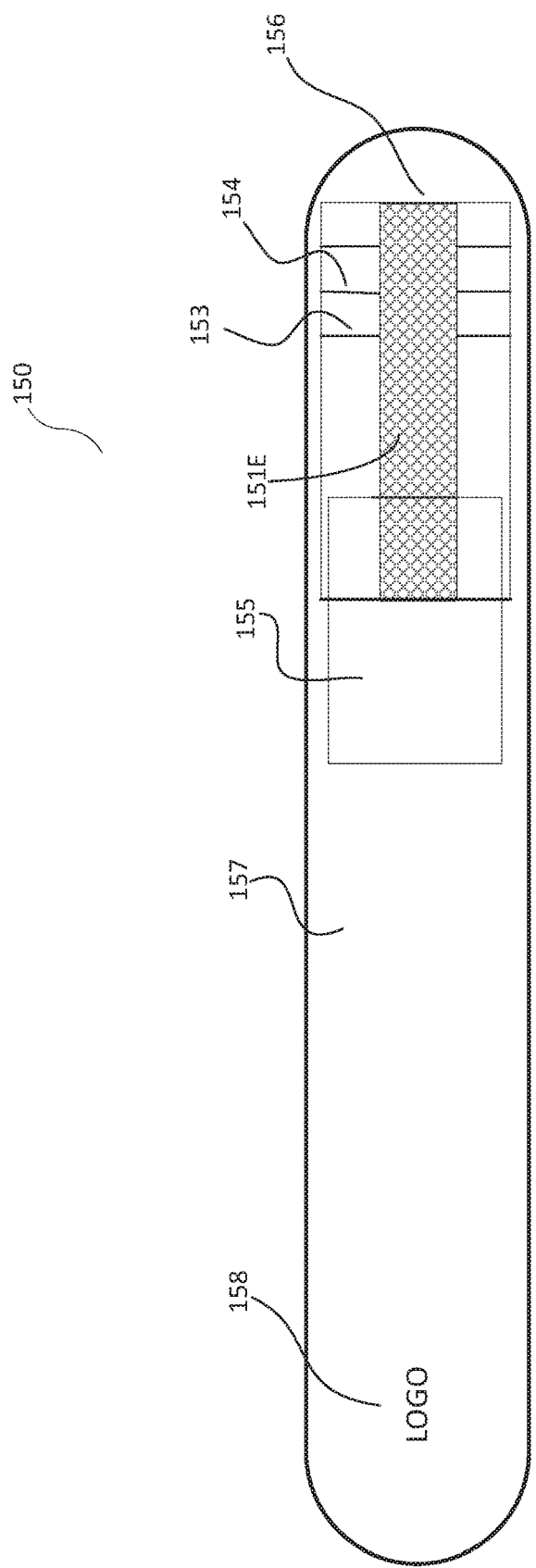

FIGS. 1F-G illustrate another embodiment 150 of a hydration sensor. The sensor includes a water-permeable material, which could be, for example, cotton, absorbing paper from wood fiber (such as paper towel and blotter paper), polyester and glass fibers. The cotton can be made into different forms, such as cheesecloth, gauze and muslin.

One embodiment includes a slice 151, with at least a piece of cotton 151A, such as cheesecloth, as a water-permeable material. In one approach, there could be more than one piece of cotton, such as two or more pieces. In the embodiment shown in FIG. 1F, there are two pieces of cotton, 151A and 151B, pressed together, to serve as the piece of water-permeable material. As an example, the two pieces of cotton together could have a combined thickness of about 10 mil. The water-permeable material can be laminated by two pieces, 151C and 151D, of at least substantially water-impermeable material, to form a segment 151E.

The segment 151E can be placed on a piece of printable material, 151F. In another embodiment, the segment 151E can be placed adjacent to a piece of printable material. The piece of printable material can be plastic or other materials that could carry a marking. In one approach, the piece of printable material can be paper. There could be markings on the printable material. In one example, the piece of printable material can have a thickness of about 4 mils. Then the segment 151E with the piece of printable material can be laminated by two pieces, 151G and 151H, of at least substantially water-impermeable material. With the lamination, the segment 151E is covered by at least substantially water-impermeable material, and is exposed to air at the two ends of the slice 151. In one example, the slice has a length of about 1.5 inches, a width of about 0.7 inches and a thickness of about 20 mils. In another example, the slice 151 can initially be much longer, and can be cut into shorter pieces at the desired length.

There can be a chemical compound on the water-permeable material. The chemical compound can change when the compound gets wet, such as changing its visual appearance. The change to the chemical compound can be observable, such as through the two pieces of at least substantially water-impermeable material, 151H and 151G.

FIG. 1F shows a cross-section of the slice 151 with the segment 151E on the printable material 151F, sandwiched between two pieces of at least substantially water-impermeable material, 151G and 151H.

A number of at least substantially water-impermeable materials have been described. They can be thin plastic sheets or films. In one example, a thin plastic sheet can have a thickness of about 1.5 mils.

FIG. 1G illustrates the top view of the embodiment 150 of the hydration sensor, with the slice 151 having the segment 151E around the middle. The slice 151 can be glued on a substrate 157. In another embodiment, the bottom side of the slice 151 can be adhesive to stick onto the substrate. In FIG. 1G, the top view also shows markings, such as 153 and 154, on the printable material 151F. The markings can be indicators regarding the hydration level of a being. There also can be a logo 158 on the substrate.

In one embodiment, the being can be a human being. In another embodiment, the being can be an animal, such as a dog or a cat.

In one embodiment, the segment 151E is exposed at its two ends. In one approach, there could be a piece of tape or other at least substantially water-impermeable material 155 covering one of the ends. The other exposed end 156 could serve as an aperture to allow saliva to reach the water-permeable material, 151A and 151B, and to the chemical compound via the water-permeable material.

In one embodiment, in addition to the chemical compound, there can be a food flavor compound on the water-permeable material. In another embodiment, the food flavor compound can be in, adjacent to, or associated with the water-permeable material. The flavor could make it easier to keep the sensor 150 in the being's mouth. For example, the flavor could be beef flavor, which dogs may prefer; tuna flavor, which cats may prefer; and cherry flavor, which children may prefer.

The substrate 157 can serve as a supporting structure for the slice 151. The substrate 157 can be rigid, malleable or flexible. For example, the substrate 157 can be a piece of thin plastic, such as ABS, Polypropylene, or glass-filled polypropylene. Other materials capable of supporting the slice 151 can be used. In one approach, the substrate is a piece of wooden stick, such as a tongue depressor, covered by at least substantially water-impermeable material or a water-proof film.

In one example, the substrate 157 has the length of about 6 inches, a width of about 0.75 inches, and a thickness of about 75 mils. In another example, for babies and small animals, such as dogs and cats, some or all of the dimensions of the hydration sensor 150 could be reduced, such as by 50% or more. In yet another example, for large animals, such as cows and horses, some or all of the dimensions of the hydration sensor 150 could be increased, such as by 50% or more.

Different embodiments of hydration sensors have been described regarding the hydration level of a being. The hydration sensors can also be applied in different areas. In one embodiment, a hydration sensor can be used to measure the water content of soil to decide if plants need to be watered. For example, one could stick the hydration sensor into the soil for a preset duration of time to measure the hydration level of the soil. In this example, the piece of at least substantially water-impermeable material 151G can be thicker than a few mils. For example, it can be a piece of plastic sheet that is 10 to 15 mils thick.

In another embodiment, a hydration sensor can be used to measure the hydration level or viscosity of paint to determine its suitability for typical paint sprayers. For example, one could stick the sensor into the paint for a preset duration of time to measure the hydration level of the paint.

In one embodiment, a hydration sensor can be used to measure if a pipe is leaking. For example, one could run the sensor at a preset pace along the pipe surface to measure the hydration level of the outside of the pipe. To illustrate, the substrate 157 can be substantially longer than 6 inches to allow the hydration sensor to go through a small hole in a wall to extend along the wall of the pipe.

In another embodiment, a hydration sensor can be used to measure the hydration level of honey. Honey typically has an extremely long shelf life if the honey reaches a certain percentage of water content, such as 17-18%. But too much water could spoil the honey. In one approach, a beekeeper could stick the hydration sensor into the honey for a preset duration of time to measure the hydration level of their honey for a proper harvest.

Figure 2:
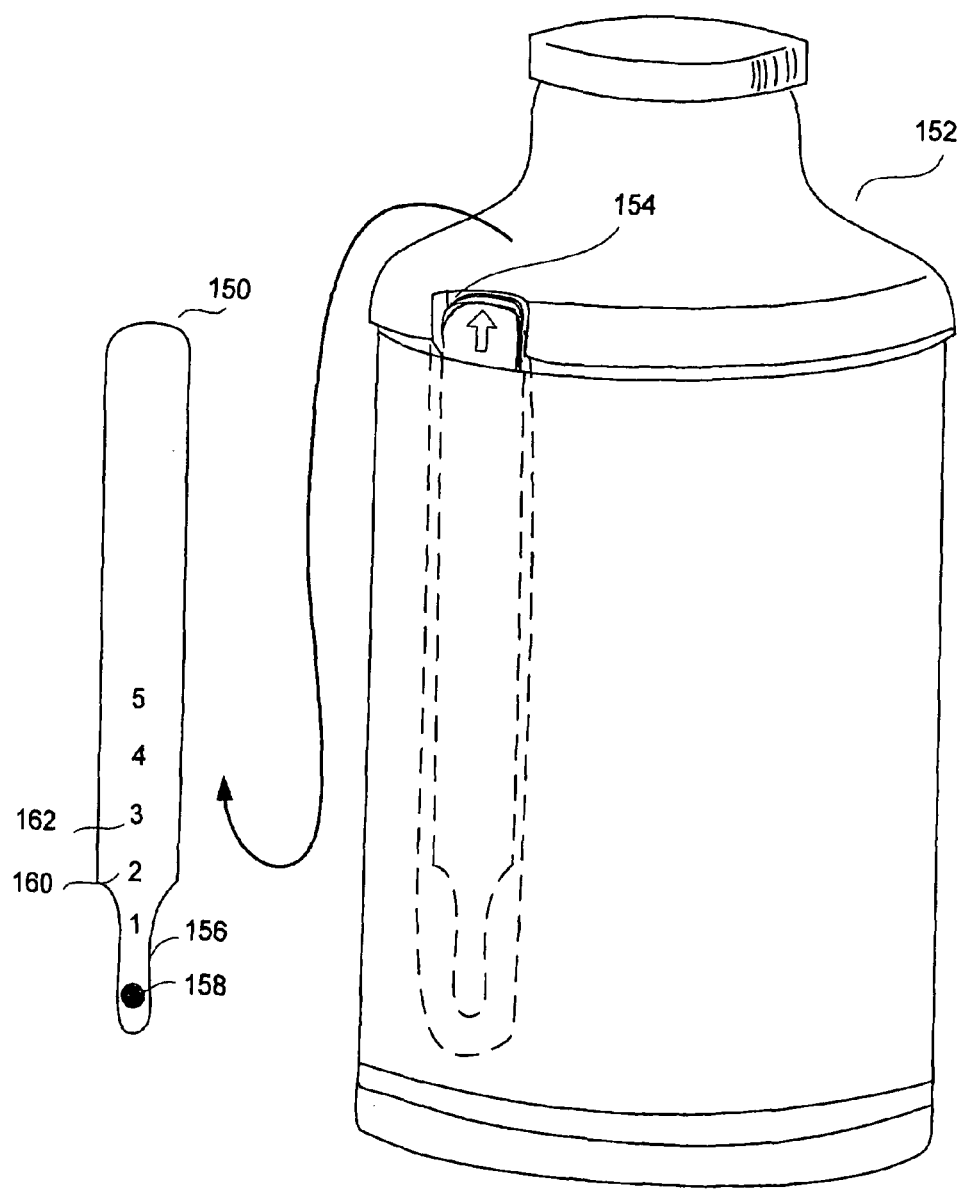
FIG. 2 illustrates an embodiment of disposable hydration sensing elements coupled to a bottle according to the invention.

FIG. 2 illustrates one embodiment of disposable hydration sensing elements 150 coupled to a bottle 152 which can carry a type of fluid or beverage. For example, the fluid can be a type of filtered water, electrolyte drinks or sports drinks, such as Gatorade®. The sensing elements 150 can be similar to the element shown in FIGS. 1C-1D. There can be a slot 154 on one side of the bottle 152 to carry the sensing elements 150. Each sensing element 150 can have a narrower section 156, which is the section to be put in the mouth of the user. An opening 158 can be provided close to the end of the narrower section 156 to receive saliva. Windows, 160 and 162, to the water-permeable material (e.g., filter paper) can be numbers, instead of just holes. Based on the measurement, one or more of such numbers can change color. For example, if only the numeral "1" changes color, the user is rather dehydrated so she should drink some fluid.

Figure 3B:
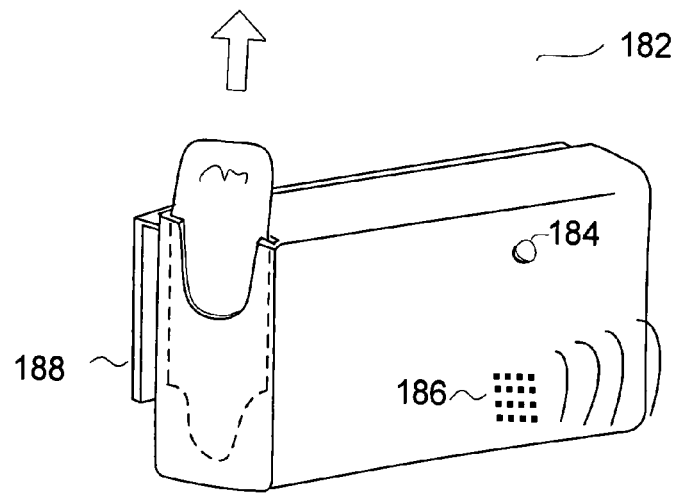
FIGS. 3A-3B illustrate an embodiment of a disposable hydration sensing element and its carrier that has a timer according to the invention.
Figure 3A:
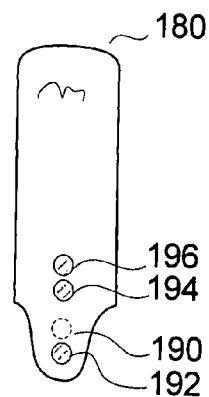

In another embodiment, sensing elements are stored in or carried by a carrier. The sensing elements with the carrier can be a hydration sensor. FIG. 3A illustrates an embodiment of a disposable hydration sensing element 180. FIG. 3B illustrates an embodiment of a carrier 182 that has, among other components, a timer, a switch 184 (such as an activation switch), an audio device 186 and a power source, such as a battery or a solar cell.

The carrier 182 shown in FIG. 3B can hold a number of the hydration sensing elements 180. In this example, the carrier 182 can be a handheld or wearable electronic device. In one embodiment, the carrier 182 can be in the shape of a box. The carrier 182 can have a mechanical device 188, such as a clip, to clamp or attach the carrier 182 onto the clothing of a user. In another embodiment, the carrier 182 can be configured into a wrist band and is carried on the wrist of the user, just like a watch. In yet another embodiment, the carrier 182 also functions as a watch and can include a display. In still another embodiment, the carrier 182 can be incorporated in or attached to a piece of clothing (e.g., helmet, hat, vest, belt, or shirt) of the user, or incorporate in or attach to a portable electronic device carried or worn by the user.

The sensing element 180 shown in FIG. 3A can be similar to the elements shown in FIG. 2 or the element shown in FIGS. 1C-1D. For example, the element 180 can have a piece of water-permeable material (e.g., blotting paper) laminated between two pieces of tape. In this embodiment, the compound that produces color patches is on the same surface of the water-permeable material as the surface that is exposed to the opening. In this embodiment, there are a number of dots of a compound, and they can be of different color and at different distances from the opening 190. When they are not wet, the compound is a very small amount of dry powder and is inconspicuous. These can be grains of powder food dye. The grains can be of different color, such as red, blue and green. When there is liquid, the dye dissolves and a color patch is formed. In FIG. 3A, there are three dots. The dot nearest 192 to the opening 190 can be red in color; the second closest 194 can be blue and the furthest away 196 can be green.

To measure hydration level, the user pulls one of the sensing elements 180 out from the carrier 182, places at least a portion of the element 180 in his mouth and then pushes the button or switch 184 on the carrier 182. This will activate the timer. After a duration of time, such as 1 minute, the timer will activate the audio device 186, such as a beeper, which would beep. This will alert the user to remove the element 180 from his mouth and read it. If only the red dot 192 shows up, the user is very dehydrated. If a red 192 and a blue 194 dots show up, then the user is mildly dehydrated. If all three dots can be seen, the user is well hydrated.

Figure 4:
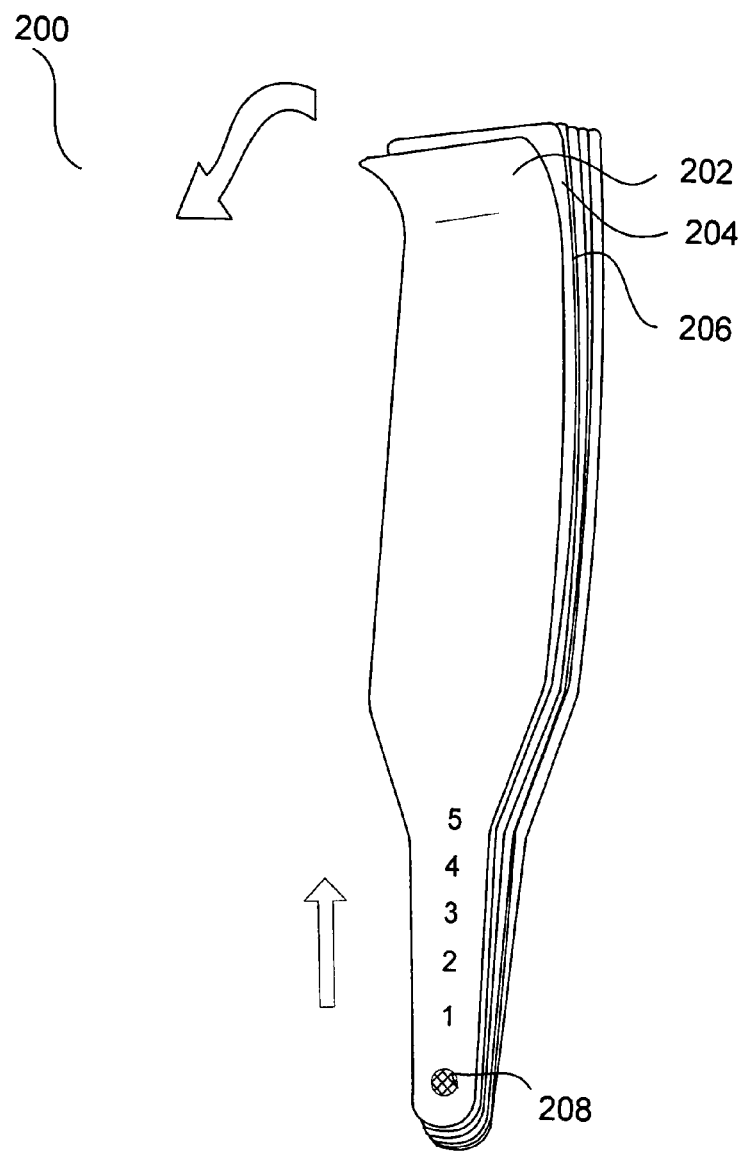
FIG. 4 shows one embodiment of multiple hydration sensing elements in a stack according to the invention.

FIG. 4 shows one embodiment 200 of multiple hydration sensing elements 202 and 204 linked, attached or stuck together into a stack. Each element, such as 202 and 204, can be similar to the element 150 shown in FIG. 2. In one embodiment, the elements 202 and 204 are glued or connected together, such as at their edges, 206. For example, this connection at the edges could provide a waterproof seal. To use each element, the user can peel one off and put it in his mouth. Alternatively, in one embodiment, the user can put the entire stack into his mouth. Saliva only goes into the top element because the only opening exposed is the opening 208 of the top element 202. After the measurement, the user can peel off the top element 202, and the opening in the next element, the element 204 beneath the top element 202, is exposed to be used.

Figure 5B:
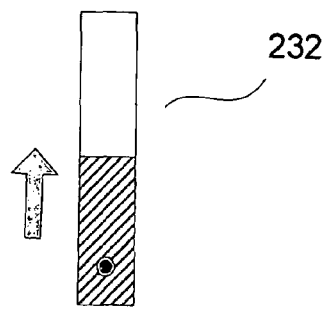
FIGS. 5A-5B illustrate an embodiment of a handheld hydration sensor that can automatically measure a disposable sensing element according to the invention.
Figure 5A:
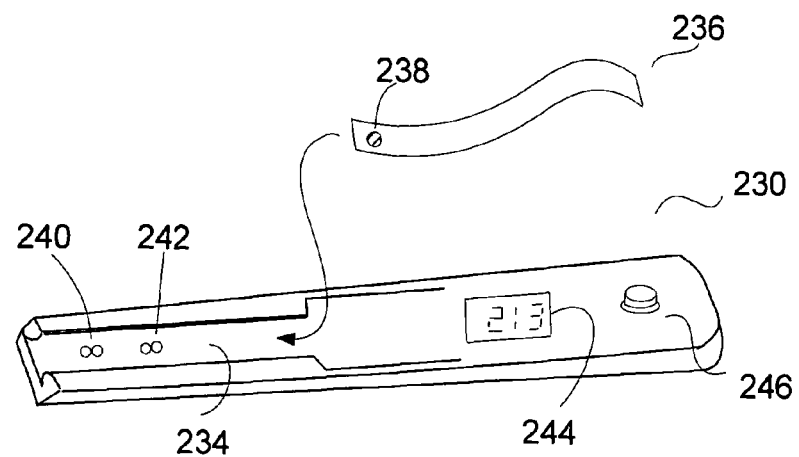

FIG. 5A illustrates an embodiment of a handheld hydration sensor 230 that can measure a sensing element. In one embodiment, the handheld hydration sensor 230 can measure a sensing element 232 such as shown in FIG. 5B.

The sensing element 232 shown in FIG. 5B can be similar to the one shown in FIG. 4, except that the water-impermeable material with the opening for saliva to get to the water-permeable material can be transparent. To take a measurement, the user places one such sensing element 236 into a slot 234 on top of the handheld hydration sensor 230. Next, the user places at least a portion (such as the narrower end) of the sensor 230 into his mouth, under his tongue, like a thermometer. The saliva in the user's mouth will permeate or wick from the opening 238 up the length of the sensing element 236, causing a color change to move up the sensing element as shown, for example, by the arrow in FIG. 5B. As shown in FIG. 5A, in the slot 234 of the handheld hydration sensor 230 there are two LED/photodiode pairs, 240 and 242, that sense the color change of the element.

Though there can be many pairs of photodiodes and photo-detectors along the slot 234, only two are shown. Each photodiode and photo-detector pair measures color change at different distance away from the opening, with the diode emitting light and the corresponding detector measuring the reflected radiation. In one embodiment, based on measuring changes in the reflected light from the different detectors, the extent that the saliva has diffused into the sensing element can be identified.

The handheld hydration sensor 230 in FIG. 5A can also include a timer 244 and a switch, such as an activation switch, 246, which can be functionally similar to the timer and switch shown in FIG. 3B. In one embodiment, the handheld hydration sensor 230 can include at least two pairs of LED/photo-detector positioned at different position in the slot 234, such as described above. The timer can track the time it takes saliva to wick up the element from the position of the first pair to the second pair. With the distance between the two pairs known, the handheld hydration sensor 230 can measure the rate the compound changes color, or the speed the color moves up the element.

A number of embodiments of hydration sensing elements have been described. They are typically based on visual measurements. They are typically more applicable for single use and can be disposable.

Figure 6A:
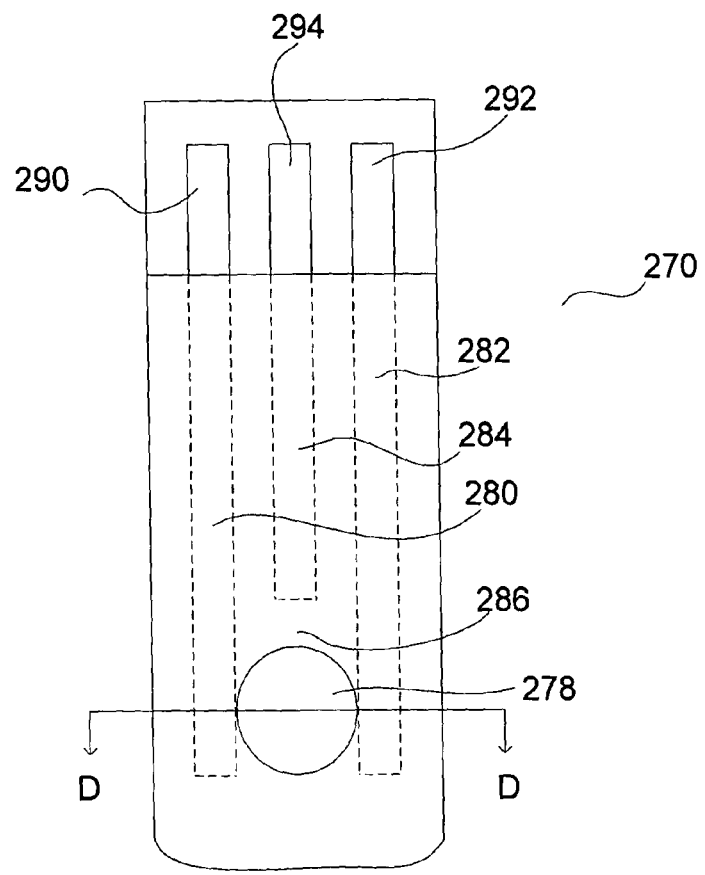
FIGS. 6A-6B illustrate a hydration sensing element applicable for more than one-time use according to an embodiment of the invention.
Figure 6B:
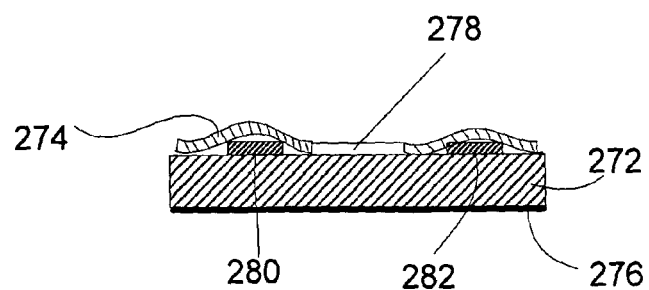

In one embodiment, a hydration sensing element uses electrical resistive measurements. The sensing element can be applicable for more than one-time use. FIGS. 6A-6B illustrate an embodiment of such a hydration sensing element 270. FIG. 6A shows the top view of the hydration sensing element 270, and FIG. 6B a cross sectional view at DD. In one such embodiment, the sensing element 270 includes a piece of water-permeable material 272, such as a piece of blotter paper, sandwiched between two pieces of water-impermeable material 274 and 276. The two pieces of water-impermeable material 274 and 276 do not have to be transparent, and they can be tape 274 and 276. The top piece of tape 274 includes an opening 278, exposing a small part of the piece of the water-permeable material 272. There are a number of electrically conducting lines on the water-permeable material 272. In one embodiment, there are two conducting lines, such as the two outer lines, 280 and 282, shown in FIG. 6A. They are covered or encapsulated by the top piece of water-impermeable material 274. Each of the lines 280 and 282 has its corresponding metal contacts, such as the left conducting line 280 has a left contact 290 and the right conducting line 282 has a right contact 292.

A user can place the sensing element 270 shown in FIG. 6A in his mouth. Saliva then goes through the opening 278 and is absorbed by the water-permeable material 272. With saliva in the opening 278, the resistance between the lines, such as lines 280 and 282, is reduced. By measuring the resistance between the lines, one can determine how wet/dry the mouth is.

The embodiment of the hydration sensing element 270 shown in FIGS. 6A-6B can be coupled to a timer, which can be in a hydration sensor. The timer can be used to measure the resistance change between the conductors as a function of time after a sensing element is placed in the mouth. For example, before the user puts the sensing element in his mouth, the user activates the timer. At that point, the water-permeable material is dry, and the resistance between the lines can be in the range of more than 10 mega-ohms. The timer starts counting after it is activated (i.e., turned on). In one embodiment, the timer can stop counting when the resistance between the lines drops below a preset threshold, for example, 1 mega-ohm. The timer records the time elapsed. In one embodiment, the timer can produce a beeping sound or a flashing LED to indicate to the user that the resistance has dropped to the preset threshold, and the hydration measurement has been completed. The user can then take the sensing element out of his mouth, and the hydration level of the user can depend on the elapsed time. In another embodiment, the elapsed time can be preset to measure the resistance between the lines. The hydration level can depend on the resistance value.

In yet another embodiment, referring to FIG. 6A, the hydration sensing element 270 includes a mechanism to initiate measuring the hydration level of the user. In this embodiment, there is a third conducting line 284 between the two outer lines 280 and 282. This third line 284 can have its own contact 294. In one embodiment, at least a portion of each of the outer electrically-conducting lines 280 and 282 is closer to the opening 278 than the third conducting line 284. For example, a small portion of the edges of the outer two conducting lines 280 and 282 are exposed to the opening, and the third conducting line 284 is recessed at a certain distance 286 from the opening 278. When the user puts the sensing element 270 into his mouth, the saliva can reduce the resistance between the outer two conducting lines 280 and 282 almost immediately. For example, a timer can start counting when the resistance between the outside lines 280 and 282 drops below a preset value. In other words, when the resistance between the two outer conducting lines is below a preset value, the sensing element 270 starts sensing the hydration level of the user. Then, as saliva continues to diffuse into the water-permeable material 272, the resistance between the middle contact 294 and the contacts of either or both of the outer conducting lines 290 and 292 drops. Again, in one embodiment, when this resistance drops, which can be to below a certain preset value, the timer stops counting.

As discussed, the water-permeable material 272 shown in FIG. 6A can be based on a piece of paper, such as blotting paper. In another embodiment, the water-permeable material 272 is a piece of cloth, such as polyester cloth. The conducting wires can be glued, sewn or integrated into the water-permeable material, such as cloth, or they can be printed with electrically conductive ink onto the material.

In another embodiment, instead of sandwiched between water-impermeable materials, like tape, the water-permeable material can be encapsulated, pressed or heat-sealed in between two pieces of harder and/or more durable materials, such as plastic strips or printed circuit boards. The strips or boards have their corresponding openings for saliva to get in. In one embodiment, the conducting wires can be on one of the strips or boards, which are coupled to or pressed against the water-permeable material, such as cloth or paper.

The hydration sensing element 270 shown in FIG. 6A can be applicable for more than one-time use. One approach is to let the sensing element 270 dry after it has been in the mouth of the user. When it is dry, the user can use the sensing element 270 again for measurement. Alternatively, the user can dip the sensing element 270 in rubbing alcohol, which would speed up the drying process and disinfect the sensing element 270. If the water-permeable material is a piece of cloth, in one embodiment, the user can more easily wash and dry it after it is used.

In one embodiment, a small amount of salt (or other types of resistance-lowering materials) is added in the water-permeable material shown in FIG. 6A, such as in between or among the lines. The resistance-lowering materials can be used to reduce the resistance measured when there is fluid, such as saliva, in between the lines.

Figure 7A:
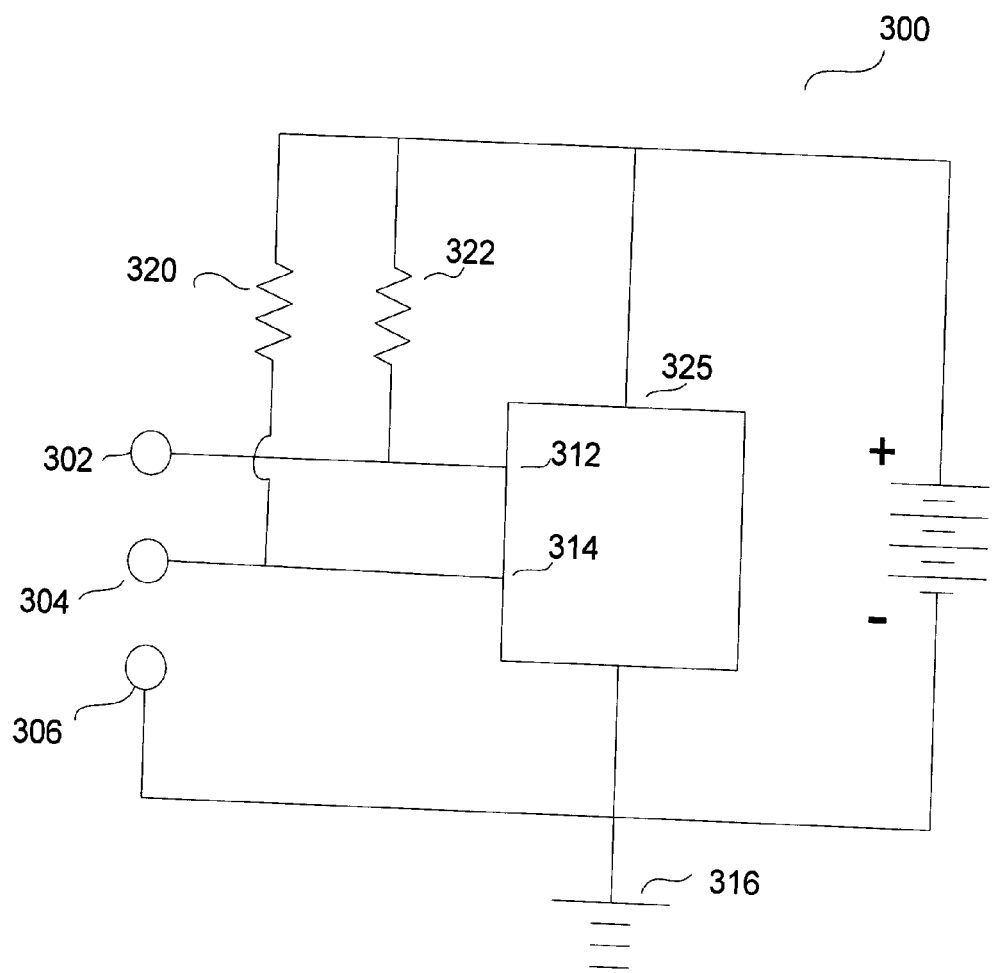
FIGS. 7A-7B show different embodiments of electrical components to measure the outputs from the sensing element shown, for example, in FIGS. 6A-B, according to the invention.

FIG. 7A shows an embodiment 300 of electrical components to measure the outputs from a sensing element, such as the sensing element 270 shown, for example, in FIGS. 6A-6B. In FIG. 7A, the three contacts, 290, 294 and 292 from the sensing element 270 shown in FIG. 6A are connected to a first input terminal 302 and a second input terminal 304 of a microcontroller unit 325 and to a ground input terminal 306, respectively. Two inputs 312 and 314 of the microcontroller unit 325 are connected to the first terminal input 302 and the second terminal input 304, respectively. In addition, the two inputs 312 and 314 are also connected to the Vcc of the microcontroller unit 325 through two resistors 320 and 322. The two resistors 320 and 322 can, for example, be 10 mega-ohm resistors. A battery is connected between Vcc and ground 316. The microcontroller unit 325 can include a counter and is programmed so that when an input signal that is lower than a first threshold value is registered between the first input terminal 302 and ground 316, the counter starts counting. This occurs when the resistance between the outer contacts 290 and 292 of the sensing element 270 drops lower than the first threshold value. The time interval between counts can be fixed. The counter stops counting when an input signal that is lower than a second threshold value is registered between the second input terminal 304 and ground 316. The number of counts is registered. As an example, assume the battery is 1.5 volts, the first threshold value is 0.75 volts and the second threshold value is also 0.75 volts. The microcontroller unit 325 can also be programmed to convert the count to a dryness level, and display the dryness level on a display. To convert the count to a dryness level, there can be a conversion table stored in the unit 325. For example, one approach can be that a count number within a certain range implies that the user is well hydrated. Such a conversion table can be determined based on calibrating the sensing element, which is further discussed below.

Figure 7B:
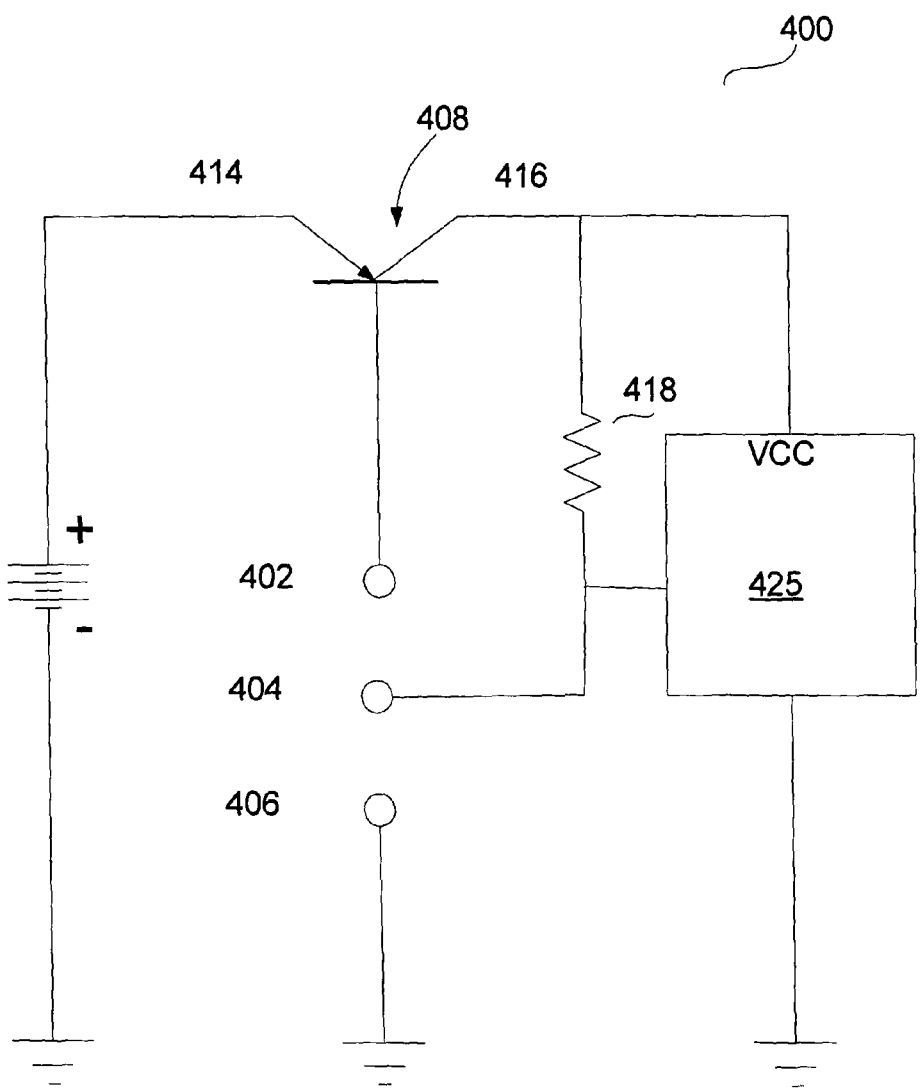

FIG. 7B shows another embodiment 400 of sensor electronics applicable for a hydration sensing element, such as the sensing element 270 shown, for example, in FIGS. 6A-6B. In this embodiment, the three contacts 290, 294 and 292 from the sensing element 270 shown in FIG. 6A are connected to the base 402 of a PNP transistor 408, an input pin 404 of a microcontroller 425, and ground 406 respectively. A battery is connected to the emitter 414 of the transistor 408 and to ground 406. A resistor 418 is connected between the input pin 404 of the controller 425 and to the collector 416 of the transistor 408, which is connected to the positive power-supply (VCC) input of the microcontroller unit 425. To illustrate, in one embodiment, the battery is 1.5 volts, and the resistor 418 is 10 mega-ohms. When the voltage between the outer contacts shown in FIG. 6A (or the voltage at the base of the transistor) reaches, for example, 0.7 volts, the transistor 408 starts to conduct, connecting the positive terminal of the battery to the VCC input of the microcontroller unit 425. This would turn on the microcontroller unit 425, and the microcontroller unit 425 would be programmed to start counting. The middle contact 294 of the sensing element 270 is connected to the collector 416 of the transistor 408 through the resistor 418. When the input at the input pin 404 of the microcontroller unit 425 reaches, for example, 0.75 volts, the unit 425 is programmed to stop counting. Again, the number of counts can be converted by the microcontroller unit 425 to a hydration level, and can be displayed.

Figure 8A:
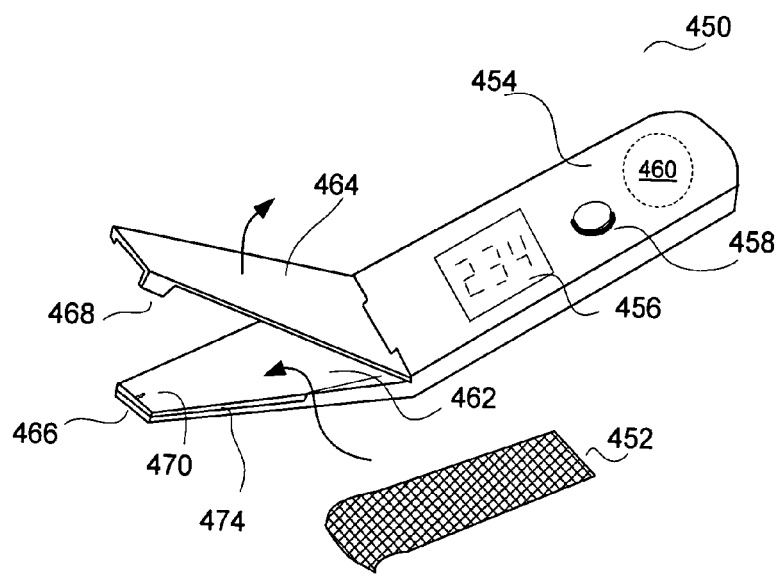
FIGS. 8A-8B show a hydration sensor applicable for more than one-time use according to an embodiment of the invention.
Figure 8B:
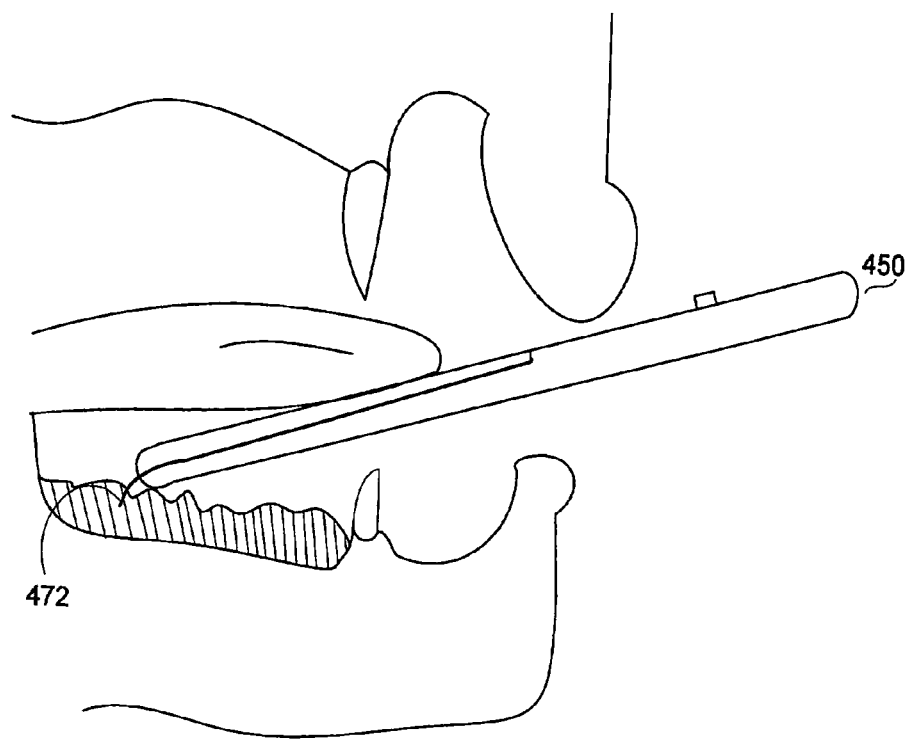

FIGS. 8A-8B show an embodiment of a hydration sensor 450 that is applicable for more than one-time use. FIG. 8A shows a hydration sensor housing 454 for the sensor 450. The sensor housing 454 includes a timer 456 (which can also function as a clock), a switch 458, such as an on/off switch, and a power source 460, such as a battery, among other electronics. The front portion of the housing 454 includes a cavity 462, which can be closed by a hinged door 464. In one embodiment, the door 464 can be locked by a clip 468 at the tip of the door 464. When the door 464 is closed, the door 464 encloses the cavity 462, except that at least one end 466 (a first end) of the cavity is not fully closed.

The cavity 462 can hold a sensing element, which, in one embodiment, is a piece of water permeable material 452. The water-permeable material 452 can, for example, be a blotting paper, or a piece of cloth, such as fiberglass cloth or polyester cloth.

In one embodiment, inside the cavity 462 there are a number of electrical contacts 470, such as three contacts, and they are positioned proximate to the first end 466 of the sensor housing 454. In one embodiment, the contacts 470 can be on the surface of a printed circuit board in the cavity 462.

The hydration sensor 450 shown in FIG. 8A can be used to measure the user's hydration level. Assume that there are a number of electrical contacts 470, such as three contacts. The contacts 470 are spaced apart, with the resistance value between the first two contacts from the first end 466 of the sensor housing 454 for starting the timer 456, and with the resistance value between the second and the third contacts for stopping the timer 456. The spacing between any two contacts can be, for example, 0.010 inches. The three contacts can be the three contacts for the circuits shown in FIG. 7A, with the first contact from the first end 466 being a ground contact, the second and third contacts going to the controller. Alternatively, the three contacts can be for the circuits shown in FIG. 7B, with the first contact being ground, the second being the contact to the base of the transistor and the third being the contact to the input of the controller.

To measure hydration level, a sensing element, such as 452, is placed inside the cavity 462, with the door 464 closed, but with a small portion of the sensing element 452 exposed from the first end 466 of the hydration sensor 450. The sensing element 452 is touching the contacts 470; this can be done by having the closed door 464 pushing the element 452 to couple to the contacts. As shown in FIG. 8B, the user inserts the hydration sensor 450 under his tongue and pushes the switch 458 to activate the sensor 450, which can activate the timer 456. The saliva from the user touches the exposed portion 472 of the sensing element 452 and wicks up into the sensing element 452. When the saliva lowers the resistance between the first and the second contacts from the first end 466 to a first preset value, the timer 456 starts counting. When the saliva lowers the resistance between the second and the third contacts from the first end 466 to a second preset value (which can be the same as the first preset value), the timer 456 stops counting. The time elapsed or the number of counts provides an indication to the hydration level of the user.

In one embodiment, to improve the electrical connection between the sensing element 452 and the contacts 470 in the sensor housing, there is an elastomer or a small spring under the door 464 in the vicinity of the contacts 470. When the door 464 is closed, the elastomer or spring presses the sensing element 462 against the contacts 470, which enhances or ensures electrical connection between the sensing element 452 and the contacts 470.

In one embodiment, the contacts 470 are close to the first end 466 of the sensor housing 454. They are much closer to the first end 466 than other edges (e.g. 474) of the sensor housing, such as the left and the right edge. This will ensure that the hydration measurement at the contacts is from saliva coming through the first end 466 of the sensor housing, and not from other edges, such as 474.

In one embodiment, the sensing element 452 shown in FIG. 8A is applicable for more than one-time use. For example, the sensing element 452 can be a piece of blotting paper. After it is used, one can allow it to dry and then use it again. In another embodiment, the sensing element 452 is a piece of cloth, such as polyester cloth. After it is used, one can wash the cloth and then use it again.

In one embodiment, there are multiple pieces of the sensing elements 452 in the sensor housing 454. For example, the sensing elements 452 can be provided in a roll. The roll or multiple pieces can be serrated so that after the user has used one piece, the user can pull out that piece (such as from the first end 466 of the sensor housing 454) and remove it at the serrated region. This also brings a new sensing element into position for a next measurement.

A number of embodiments of hydration sensors and sensing elements have been described that are disposable, and a number of embodiments have been described that are applicable for more than one-time use.

In yet another embodiment, the sensing element is re-usable. For example, the sensing element can be suitable for continual use. In one embodiment, a re-usable sensing element includes a small channel (or tube) where capillary action can bring saliva up the channel. In another embodiment, pumping action can also bring saliva up the channel. There are also at least three contacts on the inside of the channel, with, for example, the first two contacts being used to indicate starting of measurements, and, for example, the second and third contacts being used to indicate the end of the measurements. Each contact has its corresponding electrical wire as leads to allow the contacts to be measured. The plurality of contacts are spaced apart up the channel. To determine the hydration level of the user, the channel is positioned inside the mouth of the user, and the resistances between or among the contacts are measured.

Figure 9:
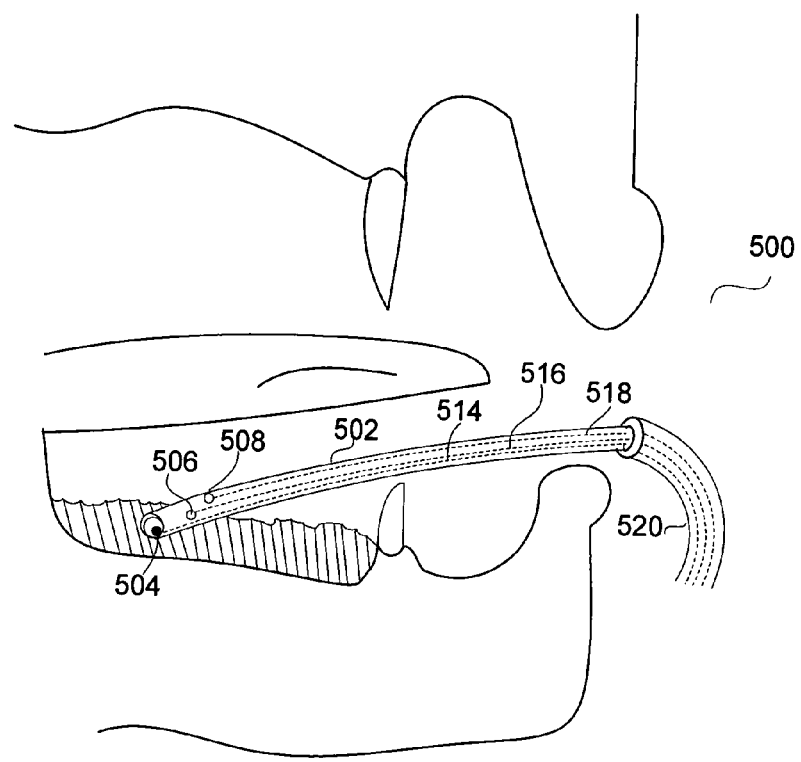
FIG. 9 shows a re-usable hydration sensing element according to an embodiment of the invention.

FIG. 9 shows an embodiment of a hydration sensing element 500 that is a re-usable type. In this embodiment, the channel of the re-usable sensor is a hollow tube 502 with a small diameter. In one embodiment, because the tube's inner diameter is small, fluid can wick up the tube based on capillary action. In one example, the tube has an inner diameter of about 9 mils. In another example, the tube has an inner diameter of about 5 mils. The tube can be made of different types of materials, such as glass, nylon, polycarbonic and acrylic. In one example, the tube is made of hydrophilic materials tended to be wetted by water, which can enhance the capillary action. Alternatively, the tube can be made of different types of materials, but coated on its inner surface with a surface coating of materials that tend to be wetted by water.

The sensing element 500 includes a number of metallic contacts. In one embodiment, there are three contacts 504, 506 and 508, with at least two of them positioned internal to the tube 502. The contacts are spaced apart up the tube 502, such as in a linear manner. As an example, the first contact 504 is close to or at the opening of the tube 502. The second contact 506 is at a certain fixed distance from the first contact 504, and the third contact 508 is further up the tube 502. Each contact is connected to a conducting wire or a conductor to electrically extend the contacts out of the tube. For example, as shown in FIG. 9, a first wire 514 connects to the first contact 504, a second wire 516 connects to the second contact 506, and a third wire 518 connects to the third contact 508. In one embodiment, for structural reasons, the wall thickness of the tube 502 increases further away from the opening of the tube. For example, in FIG. 9, the hollow tube 502 inserted inside the mouth is connected through an air-tight joint to another hollow tube 520 that has a thicker wall.

To determine the hydration level of the person, as shown in FIG. 9, a portion of the hollow tube 502 is positioned inside the mouth, probably below the tongue of the user. Then the resistance between at least two of the contacts is measured through their corresponding conductors to determine the hydration level of the user.

Figure 10B:
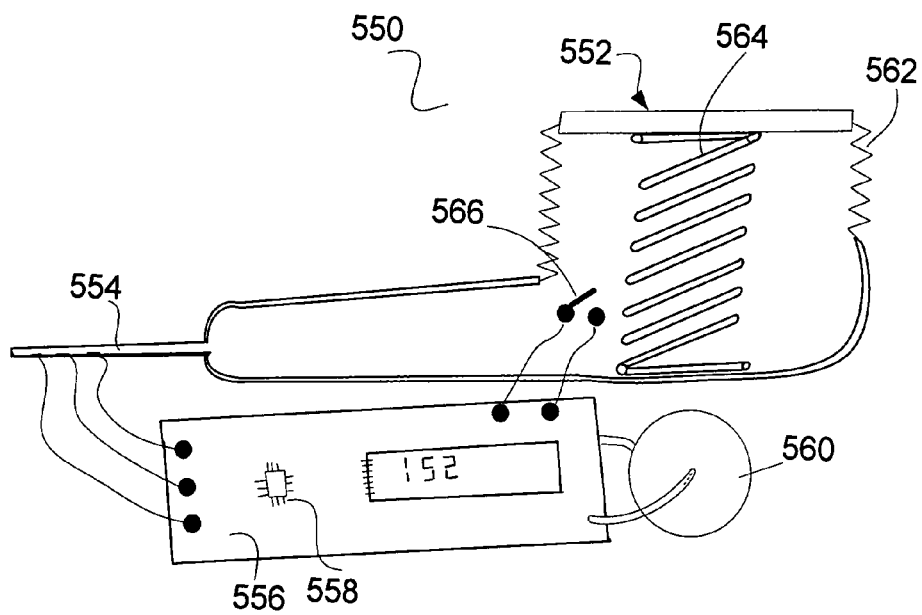
FIGS. 10A-10B show an embodiment of a re-usable hydration sensor based on a mechanical pump according to the invention.
Figure 10A:
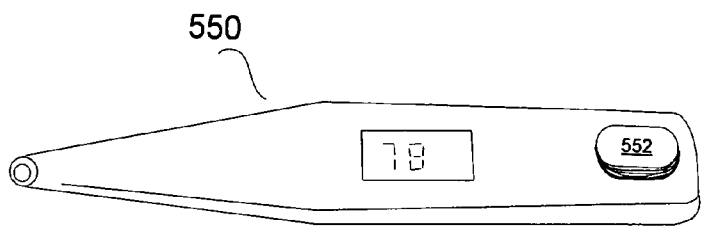

There can be different ways to clear the saliva from the tube. One approach is based on a mechanical pump. FIG. 10A shows an embodiment of a re-usable hydration sensor 550 based on a mechanical pump 552. FIG. 10B shows some of the components inside the sensor 550. As in FIG. 9, the sensor 550 includes a channel or a hollow tube 554 with a small inner diameter. Inside the tube 554, there are a number of electrical contacts. In the following example, assume that there are three contacts, similar to the three contacts in FIG. 9, with three wires from the three contacts. The three wires from the three contacts are used to measure the resistances between or among the contacts. In one embodiment, the three wires are connected to three connection points on a printed circuit board 556. In one embodiment, the circuitry on the board 556 includes those shown in FIG. 7A or 7B, with a microcontroller 558. There can also be a LCD display or other types of display for the controller 558. The sensor 550 can be operated by a small battery, such as a coin-cell battery 560.

To clear the saliva inside the tube 554 of the sensor 550 shown in FIG. 10B, the user can press a mechanical pump 552, which can be bellows 562 with a spring 564. When the bellows 562 are pressed down, air is expelled from the sensor 550, pushing any saliva out from the tube 554. In one embodiment, when the bellows 562 are pressed down beyond a certain preset point, a switch 566 is triggered, which activates the circuitry on the printed circuit board 556 to measure the resistance value between at least two contacts.

After being pressed, as the bellows 562 expands, a small vacuum is created. The flow rate of saliva up the tube 554 depends on the sucking force due to the vacuum created, the diameter of the tube and the viscosity of the saliva in the user's mouth. The time elapsed for the saliva to move, such as from the second to the third contact in the tube, is proportional to the vacuum and the saliva viscosity. The viscosity is inversely proportional to mouth hydration. By measuring the time elapsed, the sensor 550 can determine the viscosity of the saliva in the user's mouth.

In one embodiment, the pressure created by the vacuum is constant. This is accomplished through different ways, for example, by using a spring with a constant spring force, or a hollow sphere of rubber (like an eye-dropper bulb) for the bellows. To illustrate, one way to make a spring with a constant spring force is to use a long compression spring of fine spring wire (such as 8" long) and compress the spring into a short spring (such as 0.4" long). The spring force from the compressed spring is substantially constant.

In another embodiment, the pressure created by the vacuum is also measured by a vacuum pressure sensor inside the bellows for determining the viscosity of the saliva.

In one embodiment, there is a hole at the top surface of the bellows. When the bellow 562 is pressed, the finger pressing the bellow 562 covers the hole and air is pushed out of the tube 554. After being pressed, when the bellow 562 expands, the hole is exposed to suck air back into the bellow 562. With the hole being of sufficient size, no vacuum is created.

The flow rate of saliva up the tube 554 depends on the viscosity of the saliva in the user's mouth.

In one embodiment, after saliva is removed from the tube by a pump or other methods, there might be a small droplet of saliva still remaining at or hanging onto the opening of the tube. One way to remove the droplet is to wipe the opening of the tube with a piece of cloth to absorb the droplet.

In one embodiment, the sensor shown in FIG. 10B also includes a memory device and a connector. The connector could be a standard USB connector. The memory device can keep track of, for example, the hydration measurements made and the time the measurements were made. Through the connector, one can upload the measurements to another device or instrument to analyze the data. This other device or instrument can be a computer with analysis software.

In one embodiment, a hydration sensing element can be attached to the user, either directly (such as on the user's ear) or onto something worn by the user (such as the user's eyeglasses, hats or clothes). For example, the sensing element can include an attaching mechanism, such as a clip, which can attach the sensing element to the user. In one embodiment, with the element attached or worn, the tube for saliva to move or seep into is allowed to be within the user's mouth. In one embodiment, the sensing element can measure the saliva of the user continually at predetermined intervals.

In one embodiment, the sensing element can also include a wireless transceiver, which is configured to allow information related to the measurements to be wirelessly transmitted to another electronic device, such as a portable device carried by the user or someone close to the user. In one embodiment, the portable device after analyzing the measurements, wirelessly transmits an indication to the sensing element (e.g. the user needs to drink), and the sensing element can alert the user. Alternatively, the portable device directly provides the indication to the user.

In one embodiment, the portable device can transmit information related to the measurements wirelessly to a remote electronic device (as opposed to, for example, a local device, like a portable device carried by the user). The remote electronic device can be a remote station. For example, if the user is a marathon runner, a remote station can continually monitor and analyze the runner's hydration level. Based on the analysis, if the runner needs to drink, the station can wirelessly send a signal to the portable device, which can then give a signal to the runner. If the portable device is carried by a support team for the runner, the signal will be provided to the support team. The signal can be, for example, a beeping signal, a message or a blinking LED to alert the runner to drink fluid.

In one embodiment, the portable device or the remote electronic device, based on information about the climate and other information, can advise the user or his support team on how much the user should drink at the next water/fluid location. The advise can also depend on the position of water/fluid locations (or other information regarding the race) and the location of the user, which can be identified through a positioning device, such as a global positioning device, carried by the user. In one embodiment, the user's location information can be wirelessly received by the remote station as well.

In one embodiment, the sensing element is connected to a portable device or another electronic device, through a wired connection.

FIGS. 11A-11D show an embodiment of a re-usable hydration sensor 600. It can be similar to the one shown in FIG. 10A. The re-usable hydration sensor 600 can be attached to or worn in the mouth of a user. In this embodiment, the sensor 600 is inside the mouth and is configured to fit on at least one tooth of the user. In one embodiment, the sensor 600, as shown in FIGS. 11A-11D, is a bitable hydration sensor, which can remove saliva from a tube when the user appropriately bites on it.

Figure 11A:
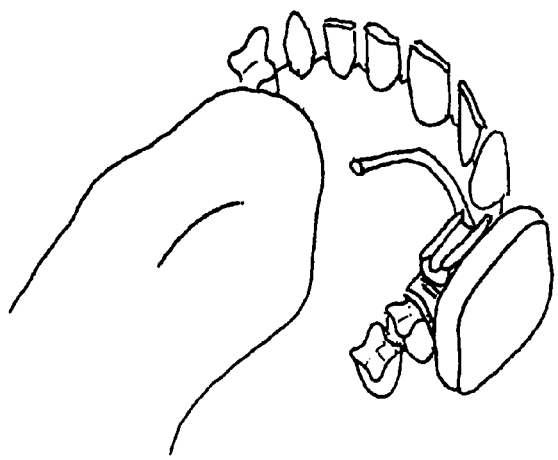
FIGS. 11A-11D show a re-usable hydration sensor clipped to the mouth of a user according to one embodiment of the invention.
Figure 11B:
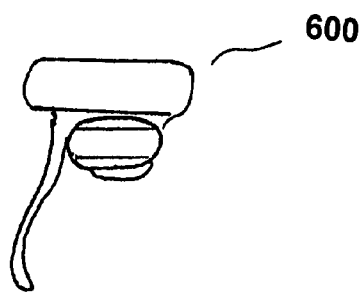
Figure 11C:
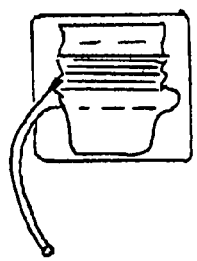
Figure 11D:
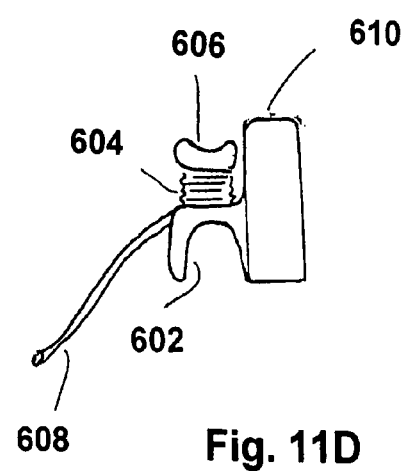

FIG. 11A shows the bitable sensor 600 inside the mouth of the user. FIGS. 11B-11D show the top, side and rear view of the bitable sensor 600, respectively. The bitable sensor 600 includes a U-shape seat 602, which in the figure is shaped to sit on the lower right first molar. On top of the seat are bellows 604, with a top cover 606. The top surface of the top cover 606 can be shaped to fit the upper right teeth of the user.

As in the embodiment shown in FIG. 10A, saliva gets into a tube 608 of the bitable sensor 600. To remove saliva in the tube, the user can bite on the bellows 604 of the bitable sensor 600. In one embodiment, when the user bites on the bellows 604, the sensor electronics are activated, such as similar to the embodiments shown in FIG. 10B. In another embodiment, the sensor electronics are activated by the tongue pushing an on/off button, which can be on a side surface of the sensor, such as there can be an on/off button on the inner side surface of the U-shape seat 602.

In one embodiment, the bitable sensor 600 further includes a casing 610 that carries circuits for a power source, such as a battery. In another embodiment, the casing also carries a wireless transmitter. After the sensor has taken measurements, the transmitter transmits the measurements to, for example, a portable device, which, for example, can be carried by the user or another. The portable device can analyze the measurements received and provide feedback to the user, such as he is fine and does not need to drink yet.

In an alternative embodiment, the sensor can be provided in the mouth, but not be bit-activated. In one implementation, the tube or channel for the sensor can be cleared by using one's tongue to depress a bellow. In another embodiment, an electro-mechanical pump can be used to clear the tube or channel of the sensor.

Instead of a mechanical pump, a re-usable hydration sensor can include an electro-mechanical pump to clear saliva from a channel or tube. Under certain condition, the pump is activated electrically to pump saliva from the user's mouth. There are different ways to set the condition. For example, the pump is turned on periodically to clear the tube. In another example, the user can activate a switch to turn on the pump.

Figure 12:
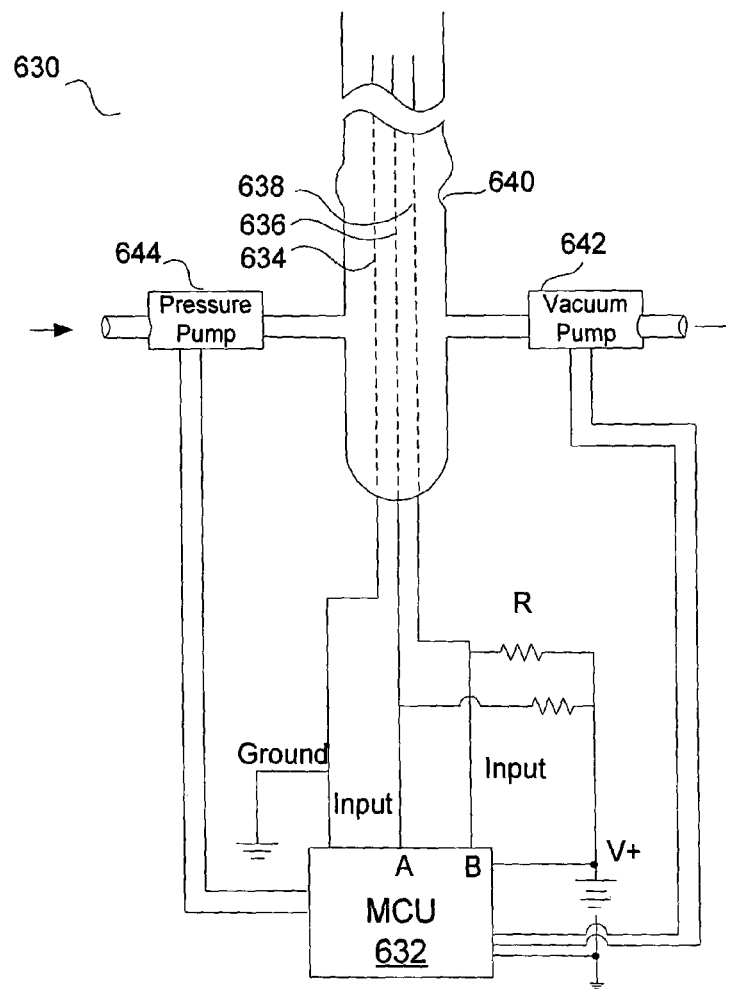
FIG. 12 shows an embodiment of different electrical components of a re-usable hydration sensor based on an electro-mechanical pump according to the invention.

FIG. 12 shows an embodiment of different electrical components 630 of a re-usable hydration sensor based on an electro-mechanical pump. Another such pump can also suck saliva into the sensor. The different conditions for activating the one or more pumps in FIG. 12 will be described in the following.

Figure 13:
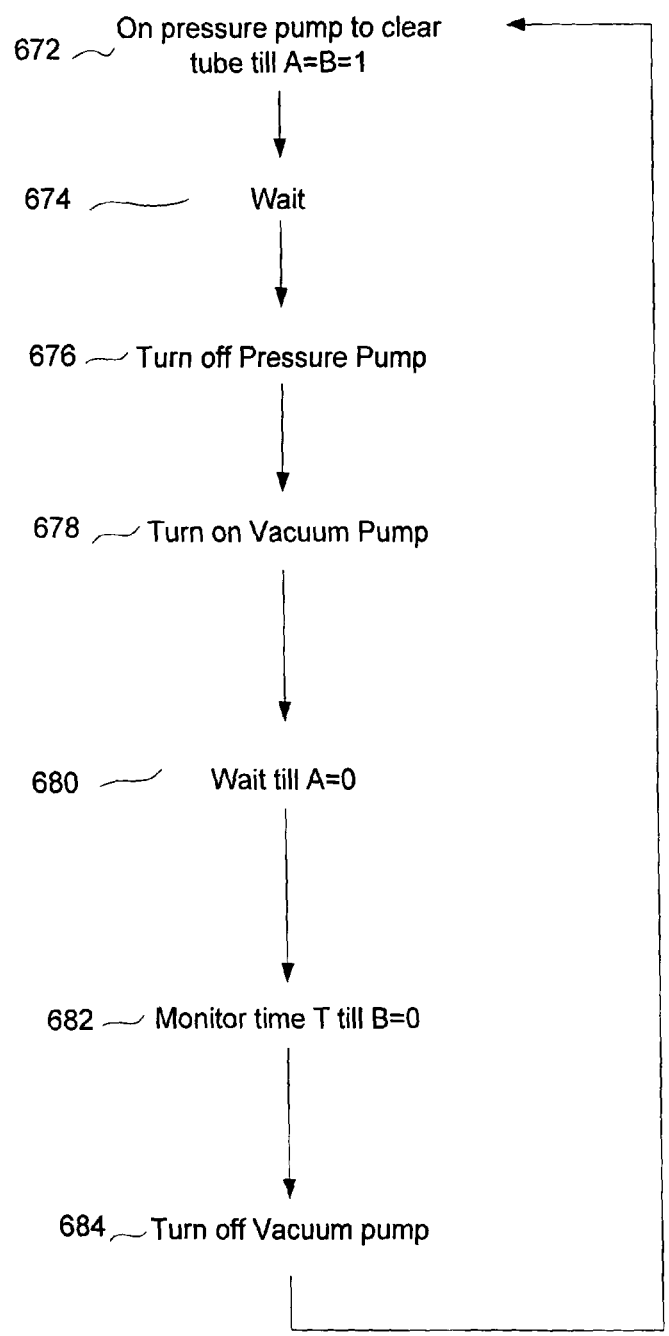
FIG. 13 shows an embodiment of a process for the hydration sensor shown in FIG. 12 according to the invention.

FIG. 12 shows three conducting wires 634, 636 and 638 leading into a microcontroller unit 632. In one embodiment, the three wires can be the three conducting wires from the three contacts of the sensing element shown in FIG. 9. In the following discussion, the three conducting wires are assumed to be three shown in FIG. 9, with 634 corresponding to 514, 636 corresponding to 516, and 638 corresponding to 518. FIG. 13 shows an embodiment of a process 670 for using the electronics of a re-usable hydration sensor such as shown in FIG. 12. First, a pressure pump 644 is turned on 672 to push air through the tube 640, which would clear saliva from the tube 640. With the saliva cleared from the tube 640, the inputs A and B received by the microcontroller unit (MCU) 632 will read high or logic 1. At this instant, saliva is substantially cleared from the tube 640 so the resistances between both the first contact and the second contact, and between the second and the third contacts in the sensing element shown, for example, in FIG. 9 are high. By keeping the pressure pump 644 on for a preset amount of time, the tube 640 remains clear during that period. This amount of time can depend on how often the MCU 632 takes measurements. After waiting 674 that period, the MCU 632 turns off 676 the pressure pump 644 and turns on 678 a vacuum pump 642. The MCU 632 then waits 680 till the reading in its input A becomes low (logic 0). At this instant, the resistance between the first and the second contact, through the first 634 and the second 636 conducting wires, is low (or below a preset value) due to the saliva provided between the contacts. Then the MCU 632 monitors 682 the amount of time "T" till its input B also becomes low (logic 0). At this point, the resistance between the second and the third contacts, through the second 636 and the third 638 conducting wires, is low (or below a preset value), again due to the saliva provided between those contacts. Then the MCU 632 turns off 684 the vacuum pump 642. This time T is proportional to the pressure of the vacuum pump and the viscosity of the saliva. The viscosity inversely depends on how well hydrated the user is. The process 670 is repeatable.

In an embodiment that uses a vacuum pump to pull saliva up a tube or channel, the tube or channel uses hydrophobic materials, which can be more easily cleaned and dried for subsequent use. Examples of materials for the tube or channel include polypropylene or polyethylene.

In one embodiment, the embodiment 630 shown in FIG. 12 does not include a vacuum pump 642. After a preset amount of time of the pressure pump 644 being on, the MCU 632 turns off the pressure pump 644. Saliva, if there is any, moves up the tube 640 by capillary action. The MCU 632 then waits till the reading in its input A becomes low (logic 0). At this instant, the resistance between the first and the second contact, through the first and the second conducting wires, is low (or below a preset value) due to the saliva provided between the contacts. Then the MCU 632 monitors the amount of time "T" till its input B also becomes low (logic 0). At this point, the resistance between the second and the third contacts, through the second and the third conducting wires, is low (or below a preset value), again due to the saliva provided between those contacts. This time T is proportional to the viscosity of the saliva, which inversely depends on how well hydrated the user is. The process can be repeated.

Instead of using a pressure pump and a vacuum pump, in another embodiment, the user can blow into the tube to clear the tube. The MCU can measure the time T without needing the pumps.

A number of re-usable sensing elements have been described where there is a small channel, such as in a small tube. In one embodiment, the small channel with electrical contacts is formed using a printed circuit board. There can be a printed circuit board and another board with a trough on one side.

There are different ways to make the board with a trough. For example, a trough can be made as the board is injection molded, by making the trough a feature in the injection mold. Another way to make the trough can be by a milling machine. To illustrate, for example the cross section of the trough is rectangular in shape, whose height and width dimensions are in the order of 5 mils. The board with the trough can be made of thermal plastic or other types of materials, such as silicone or Teflon. The board with the trough can also be, more generally, considered a trough in a substrate. In one example, the substrate can be a type of dielectric material. In another example, there can be a coating over the materials at least in the trough area where the coating tends to be wetted by water.

Regarding the printed circuit board, a number of conducting lines are formed on it. They can function as the conducting wires shown in FIG. 9, such as 514, 516 and 518. Then an insulating layer is formed over the lines. This layer can be a plastic layer on the printed circuit board, such as a solder mask. There are holes in the insulating layer for contacts. The conducting lines in the vicinity of the holes can be gold plated, and they can serve as contacts. These contacts can function as the contacts in FIG. 9, such as 504, 506 and 508. The gold plating helps prevent corrosion.

The two boards are then joined together, with the trough aligned to the contacts. There are different ways to join the boards together, such as by ultrasonic welding, adhesives or using screws. In another embodiment, the boards are joined together using a double-sided sticky tape, with the tape having a hole in the area of the trough. If the trough is rectangular in cross-section, the walls of the trough can serve as three of the sides, with the printed circuit board serving as the final side of the channel.

In yet another embodiment, a small channel is formed using tapes. For example, after forming the conducting lines on a board, two pieces of tapes are put on the board to serve as the side walls of the channel. Then a piece of acrylic is put on top of the tapes. Different means can be used to hold the structure together. For example, the tapes are double-sided sticky tapes; glue can be applied onto the top of single-sided sticky tapes; or glue can be applied onto the edges of the structure to hold it together. The boundaries of the channel would be the board, the tapes and the acrylic, with the board and the acrylic forming two surfaces and the tapes forming the side walls. The thickness of the tapes determines the height of the channel. In one example, the thickness of the tapes is 2 mils and the width of the channel is 100 mils. Instead of using tapes as the side walls of the channel, in one embodiment, solder mask or paint is used as the side walls of the channel.

In another embodiment, the piece of acrylic can be molded with two ribs or rails, which serve as the side walls, and which are placed against the circuit board. The structure can be secured with glue on the outside. In this embodiment, one surface and the two sides or walls of the channel are formed by the acrylic piece, and the other surface is formed by the circuit board.

In one embodiment, one or more of the walls or surfaces of the small channel or tube are textured. A matte surface can be more hydrophilic. As an example, at least a portion of the channel is made of acrylic, and the acrylic walls or surfaces are textured. Also, when the matte surface is wet, it is transparent, and when it is dry, it is translucent. Depending on whether an area is transparent or translucent, one can determine whether saliva has moved into the area.

In another embodiment, a small channel can be opened and closed. For example, the channel can be opened by the action of a lever, and closed by the action of a spring. In this example, one can open the channel to wipe it clean and to have it dried.

A number of re-usable hydration sensing elements have been described, each having a channel for saliva to get in. In one embodiment, after such a sensing element has been used, the channels can be cleaned using alcohol, such as rubbing alcohol. For example, the opening of a channel can be immersed in alcohol for a duration of time. By, for example, capillary action, the alcohol goes up the channel.

Then the opening of the channel is removed from the alcohol. In one embodiment a pressure pump can be used to remove alcohol from the channel. In another embodiment, the alcohol in the channel is removed by evaporation. The user can perform this operation a few times if desired to further clean the channel.

In yet another embodiment, a hydration sensing element can be based on piezoelectric effect. For example, the element includes a piezoelectric element coupled to a piece of absorbent medium, such as a thin sponge. The medium expands and gets heavier when it absorbs fluid. As the medium expands, the element is flexed, and its electrical impedance changes. The impedance of the piezoelectric element is measured, for example, at an AC frequency by an impedance measuring circuit. The AC frequency can be, for example, approximately 3 kilohertz. The degree of change depends on the expansion of the medium, which depends on the amount of fluid the medium absorbs. The amount absorbed in turn is a function of the viscosity of the saliva in the mouth. Thus, by measuring the impedance or the change in impedance as a function of time, one can determine the dryness of the mouth. To measure the swelling of an absorbent medium using a piezoelectric cantilever over the medium is known in the art, and will not be further described. In one embodiment, such a hydration sensing element is used in a hydration sensor. The sensor can further include different electrical components, such as a controller, a display, a switch and a power source. The controller can monitor the measured impedance or the change in impedance, and convert the monitored results to hydration level, which can be displayed accordingly. The sensor can be handheld, attachable to or mounted on the user, according to different embodiments.

Another type of hydration sensing element that is based on measuring the viscosity of fluid is described in U.S. Pat. No. 6,584,831, which is hereby incorporated herein by reference. This type of element can be incorporated into different types of sensors, as previously described.

In one embodiment, a hydration sensor or a hydration sensing element as previously described is calibrated for a user. After the calibration is performed, that type of sensing element or that sensing element can be personalized to the user.

Figure 14:
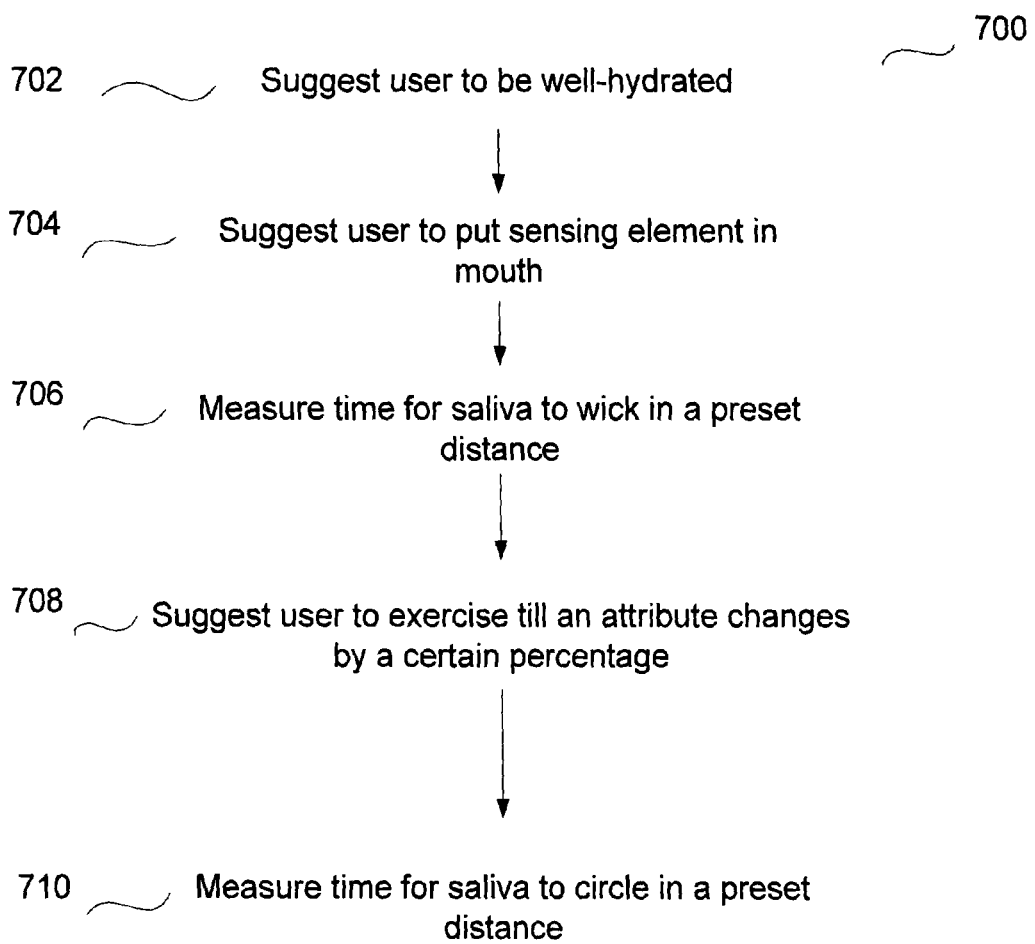
FIG. 14 shows a process to calibrate a hydration sensor according to one embodiment of the invention.

In the following, the sensing element, such as the one shown in FIG. 6A with three conducting lines, is used as an example, though other hydration sensing elements or sensors are applicable. The calibration method can be implemented by a computing device, which can be a handheld device. FIG. 14 shows one embodiment of a calibration process 700.

First, the method 700 suggests 702 the user to be well-hydrated. This can be accomplished, for example, by asking the user to drink 8 ounces of fluid every 2 hours until his urine is clear. When the urine is clear, the user is assumed to be well-hydrated. The suggestion can be through voice, visual or audiovisual techniques from a computing device. Then the method suggests 704 the user to put the sensing element into his mouth, and measures 706 the time T it takes for the user's saliva to wick a preset distance. This can be by measuring the time T when the resistance between the middle conducting line and either or both of the two outer conducting lines drops to a preset value. This time T becomes the reference time or base line of the user. It can be used to indicate the user to be well hydrated. The method then suggests 708 the user to exercise till a user's characteristic changes by a certain percentage. At that point, again the method measures 710 the time T1 for the user's saliva to wick a preset distance, which can be the same preset distance as last time. The method or process can ask the users to continue to exercise until the certain characteristic changes by a second preset value. Again perform the time measurement for the user's saliva to wick the preset distance. This third time T2 will be the time indicating the user is dehydrated to a point where the user's characteristic has changed by the second preset value. This process can repeat by continuing to ask the user to exercise. After the measurements, the sensor is calibrated for the user. Note that instead of measuring the time for a preset distance of wicking, in another approach, the method can measure the distance wicked for a preset amount of time.

In the calibration process, the user's characteristic or attribute can be the user's weight. As an example, the user can ride a stationary exercise bicycle for a duration of time, such as 15 minutes. Then, the user gets off the bike, removes sweat with a towel and measures his weight with an accurate scale. The user keeps doing this until his weight drops by such as a certain percentage. The time T1 can indicate that the user is dehydrated to the point where the user has lost 0.5% of weight, and the time T2 is where the user's weight loss is 1%. In the future, by measuring the time for saliva to wick the preset distance, the sensing element would be able to indicate how much fluid relative to the person's weight the user needs to drink just to replenish his weight loss due to, for example, dehydration.

Instead of using weight loss, in another embodiment, another attribute of a user can be measured to calibrate a hydration sensor. For example, instead of measuring weight loss, the body temperature of the user is measured to calibrate a hydration sensor.

The calibration process can be performed with respect to a type of sensing element for a group of users. The group of users might have certain similar characteristics because the calibration results might depend on the certain similar characteristics of the users, such as weight and age. For example, all of them are normal-weight adults, or all of them can be 30% over weight. Using the same approach as above, for example, in FIG. 14, the method averages the time measured for all of the users at each step. For example, the average time T1 would be the time indicating a user in that group using that type of sensing element being dehydrated by 0.5% of the users' weight. Then, in the future, by measuring the time for saliva to wick the preset distance for that type of sensing element and for users with the similar characteristics, the sensing element would be able to indicate how much fluid relative to a user's weight that the user needs to drink just to replenish his weight loss due to, for example, dehydration.

In one calibration process, a timer measures the time elapsed for a fixed distance wicked by saliva. This process is applicable for many of the different types of sensing elements and sensors previously described, such as the ones shown in FIGS. 1C, 2, 3A, 4, 5B. In yet another embodiment, instead of measuring time elapsed for a fixed distance wicked by saliva, a hydration sensing element can measure the distance wicked by saliva during a fixed time. This approach is applicable, for example, for the sensing elements or sensors shown in FIGS. 1C, 2, 4 and 5B.

In one embodiment, a hydration sensor includes a hydration sensing element to determine the optimal amount of fluid a user should consume in order for the user to be well-hydrated. The sensing element can have been calibrated by a method as described above. Then, based on measuring the hydration level of the user with the element, the sensor determines the optimal level of fluid the user should consume for the user to be well hydrated, and provide a recommendation to the user.

Figure 15:
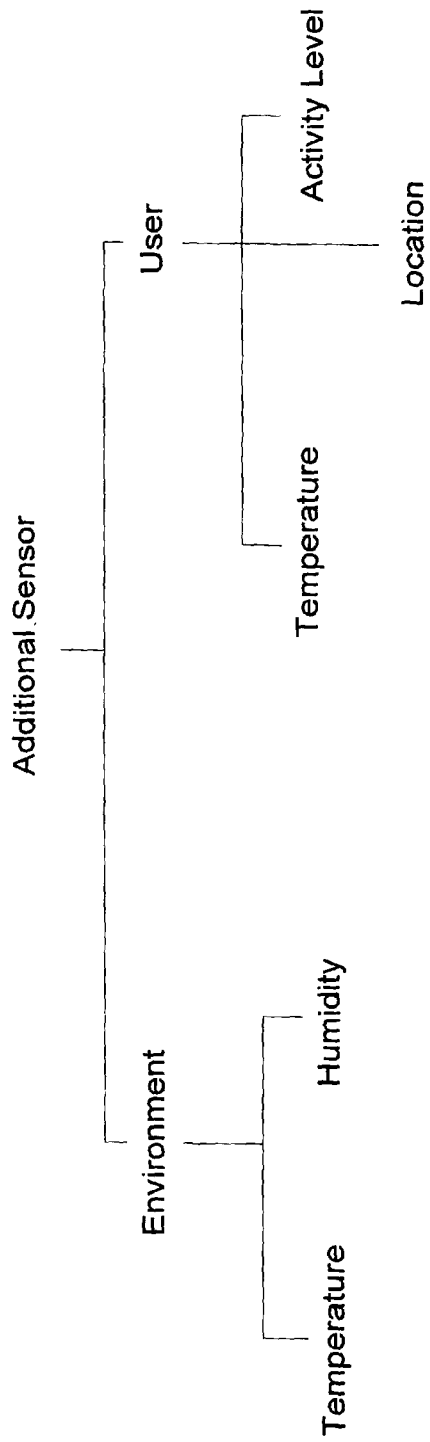
FIG. 15 shows examples of additional sensors applicable for appropriate hydration measurements according to different embodiments of the invention.

In another embodiment, the optimal amount of fluid to be consumed for a user can also depend on other factors of the environment a user is in. For example, a hydration sensor includes a hydration sensing element (such as one of the elements disclosed) and an environmental sensor that senses an attribute of the environment the user is in. FIG. 15 shows examples of environmental sensors applicable for appropriate hydration measurements according to different embodiments. For example, a temperature sensor can be configured to measure the temperature of the environment where the user is in, and the sensor is coupled to a hydration sensing element. As another example, a humidity sensor (coupled to a hydration sensing element) is configured to sense the humidity of the environment of the hydration sensing element. Based on one or more of these additional environmental sensors, the hydration sensor determines the optimal amount of fluid the user should consume. In one embodiment, after the determination, the sensor provides a recommendation to the user. The recommendation can be, for example, visual or audio.

In yet another embodiment, the optimal amount of fluid to be consumed can depend on one or more additional attributes regarding the user, other than the hydration level of the user. In one embodiment, a hydration sensor includes a hydration sensing element (such as one of the sensing element as disclosed) and a user-attribute sensor that measures an attribute of the user other than the user's hydration level. The optimal amount of fluid the user should consume depends on both the measurements by the hydration sensing element and by the user-attribute sensor. For example, one user-attribute sensor is a temperature sensor for sensing the temperature of the user. Another is a position sensor for identifying the location of the user. Yet another example for a user-attribute sensor is an activity sensor, such as a pedometer, for sensing the activity level (or the lack of activity) of the user.

Information from such one or more additional sensors can be used to adjust the signal for the user or to help determine the appropriate amount of fluid the user should consume. For example, if the temperature is around 72 degrees Fahrenheit, the time as measured by a hydration sensor indicating that the person needs to replenish 0.5% of his body weight of fluid is T1. If the temperature of the environment is high, such as more than 100 degrees, the hydration sensor automatically shortens the time based on a predetermined value.

As shown in a number of embodiments, such as the one shown in FIG. 1B, at least one surface of the sensing element can be made of a piece of opaque materials. In one embodiment, promotional materials or different designs can be printed on that surface. In another embodiment, there can be promotional materials on the sensor. In yet another embodiment, promotional materials can be on a bottle coupled to a hydration sensing element, such as the one shown in FIG. 2.

In one embodiment, the hydration sensing element or sensor is incorporated into a structure that is in the shape of, such as, a spoon, a small cup, or a small container. To use such a sensor or sensing element to measure a user's degree of hydration, as an example, the user spits his saliva into the sensor, such as in the shape of a spoon, to measure the saliva.

In one embodiment, the hydration sensing element, such as the one shown in FIGS. 1A-1D, can be incorporated into a holder of a specific configuration, such as a handle or a stick. For example, a user can hold onto the holder with the sensing element attached to one end of the holder.

In one embodiment, there is a RFID tag coupled to or integral with a hydration sensor or sensing element. The tag can be used to provide, for example, an identification of the sensor, or the tag can be used to transmit wirelessly measurements from the sensor to another device.

In one embodiment, a hydration sensor also provides recommendation to a user using it to be aware of other factors that can affect hydration measurements. For example, an audio signal can tell the person to avoid eating food such as candies or chewing gums, or drinking any beverages, right before taking measurements because such food or water might affect saliva flow, which in turn would distort the hydration measurements.

A number of embodiments have been described where saliva flows into a channel, which can be a minute channel, through capillary effect. Other embodiments have also been described where saliva flows into a channel with the assistance of a vacuum pump, which can be a mechanical or electro-mechanical pump. In one embodiment, with the pump, the dimension of the channel can be larger because saliva flows up the channel not just based on capillary effect.

One or more types of hydration sensing elements or sensors can be used to provide an absolute index on the hydration level of a user. One approach to determine absolute index based on a sensing element is to compare the known viscosity of certain liquids (known standards) with the measured results. A standard curve can be obtained from the viscosities of the known standards. The measured results are then fitted to the standard curve to determine an equation or to create a table that correlates the measured results to the standard curve. In the future, based on the equation or the table, the absolute viscosity value can be determined from the sensor measurements.

Certain disease can also affect the accuracies of the measurements. For example, a person with dry mouth or xerostomia may not give accurate result. Xerostomia could be due to genetic, radiation therapy, blood-pressure medication and autoimmune diseases. In one embodiment, a hydration sensor would warn or alert the user that if the user has sicknesses such as dry mouth, the measurements may not be an accurate measurement of his hydration level.

In yet another embodiment, a hydration sensor or sensing element, such as one or more of the previously described ones, is used for measuring symptoms related to the disease xerostomia or dry mouth of a user. Typically, the normal flow rate of saliva in an unstimulated manner is about 0.3 to 0.5 mL/minute. Values less than 0.1 mL/min are typically considered xerostomic. Flow rate and viscosity are related. In one embodiment, by measuring viscosity using, such as a viscosity sensor or sensing element as described, one can tell if a person has xerostomia. In another embodiment, the sensor or sensing element has previously been calibrated by a method as described, and the calibration can be for the person being measured.

In one embodiment, a hydration sensor or a hydration sensing element electrically couples to a bottle. In another embodiment, different electrical components in the sensor or sensing element can be incorporated in the bottle. Different embodiments regarding electrical components in a bottle have previously been described in one or more of the related patent applications identified above and incorporated by reference.

The various embodiments, implementations and features of the invention noted above can be combined in various ways or used separately. Those skilled in the art will understand from the description that the invention can be equally applied to or used in other various different settings with respect to various combinations, embodiments, implementations or features provided in the description herein.

A number of embodiments of the invention can be implemented in software, hardware or a combination of hardware and software. A number of embodiments of the invention can also be embodied as computer readable code on a computer readable medium. The computer readable medium is any data storage device that can store data which can thereafter be read by a computer system. Examples of the computer readable medium include read-only memory, random-access memory, CD-ROMs, magnetic tape, optical data storage devices, and carrier waves. The computer readable medium can also be distributed over network-coupled computer systems so that the computer readable code is stored and executed in a distributed fashion.

Numerous specific details are set forth in order to provide a thorough understanding of the present invention. However, it will become obvious to those skilled in the art that the invention may be practiced without these specific details. The description and representation herein are the common meanings used by those experienced or skilled in the art to most effectively convey the substance of their work to others skilled in the art. In other instances, well-known methods, procedures, components, and circuitry have not been described in detail to avoid unnecessarily obscuring aspects of the present invention.

Also, in this specification, reference to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams representing one or more embodiments of the invention do not inherently indicate any particular order nor imply any limitations in the invention.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A disposable hydration sensing element for measuring the hydration level of a user based on the user's saliva, the sensing element comprising:
    a sheet of water-permeable material having a first side and a second side, with a chemical compound coupled to the water-permeable material;
    a first sheet of water-impermeable material coupled to the first side of the water-permeable material; and
    a second sheet of water-impermeable material coupled to the second side of the water-permeable material,
    wherein the hydration sensing element includes at least one aperture to allow saliva to reach the chemical compound from the at least one aperture,
    wherein the chemical compound, at least due to contact with saliva, changes at least a portion of the water-permeable material, and the change is observable from at least a portion of one of the sheets of the water-impermeable material, and
    wherein the disposable hydration sensing element further includes an indicator to provide an indication regarding the hydration level of the user, based on time duration regarding the observable change of the water-permeable material, if at least a portion of the at least one aperture is placed in contact with the saliva of the user.

2. A disposable hydration sensing element as recited in claim 1, wherein the at least one aperture includes at least an edge of the water-permeable material that is exposed so that saliva is allowed to reach the chemical compound from the edge, or an opening on the first or the second sheet of water-impermeable material so that saliva is allowed to reach the chemical compound through the opening, if the at least a portion of the at least one aperture is placed in contact with the saliva of the user.

3. A disposable hydration sensing element as recited in claim 1,
    wherein the disposable hydration sensing element is connected to a plurality of similar elements to form a stack, and
    wherein each of the elements of the stack is to be used individually for measuring hydration level.

4. A disposable hydration sensing element as recited in claim 1, wherein the chemical compound is put on one of the sides of the water-permeable material and the indicator is on the other one of the sides of the sheet of water-permeable material.

5. A disposable hydration sensing element as recited in claim 1,
    wherein the indicator includes a plurality of identifiers, with each identifier spaced from the aperture by a different amount,
    wherein at least one of the two sheets of the water-impermeable material is substantially transparent at least in the area of the indicator,
    wherein the chemical compound is a powder,
    wherein the change includes forming a color patch on the water-permeable material at least due to the chemical compound on contact with saliva,
    wherein the color patch is observable at least via the sheet of water-permeable material with a substantially transparent area, and
    wherein the hydration level of the user depends on the identifier furthest away from the aperture that the color patch reaches, if the at least a portion of the at least one aperture is placed in contact with the saliva of the user for a predetermined duration of time.

6. A disposable hydration sensing element as recited in claim 1 further comprising a handle.

7. A disposable hydration sensing element as recited in claim 6 wherein the length of the handle depends on an attribute of the user.

8. A hydration sensor for measuring the hydration level of a user based on the user's saliva, the hydration sensor comprising:
    a digital timing device; and
    a disposable sensing element including:
        a sheet of water-permeable material having a first side and a second side, with a chemical compound coupled to the water-permeable material;
        a first sheet of water-impermeable material coupled to the first side of the water-permeable material; and
        a second sheet of water-impermeable material coupled to the second side of water-permeable material,
        wherein the hydration sensing element includes at least one aperture to allow saliva to reach the chemical compound from the at least one aperture,
        wherein the chemical compound, at least due to contact with saliva, changes at least a portion of the water-permeable material, and the change is observable from at least a portion of one of the sheets of the water-impermeable material, and wherein the hydration sensor includes an indicator to provide an indication regarding the hydration level of the user, based on time duration measured by the digital timing device, regarding the observable change of the water-permeable material, if at least a portion of the at least one aperture is placed in contact with the saliva of the user.

9. A hydration sensor as recited in claim 8, wherein the at least one aperture includes at least an edge of the water-permeable material that is exposed so that saliva is allowed to reach the chemical compound from the edge, or an opening on the first or the second sheet of water-impermeable material so that saliva is allowed to reach the chemical compound through the opening, if the at least a portion of the at least one aperture is placed in contact with the saliva of the user.

10. A hydration sensor as recited in claim 8, wherein at least the digital timing device of the sensor is in a carrier, which includes a mechanical device to attach to the user.

11. A hydration sensor as recited in claim 8 further comprising a plurality of other disposable sensing elements connected to the disposable sensing element to form a stack,
wherein the plurality of other disposable sensing elements are similar to the disposable sensing element, and
wherein each of the elements of the stack is to be used individually for measuring hydration level.

12. A hydration sensor as recited in claim 8 further comprising another sensor to measure either another attribute of the user or an attribute of the environment where the user is in, wherein the indication regarding the hydration level of the user is also based on measurements from the another sensor.

13. A hydration sensor as recited in claim 8, wherein the chemical compound is put on one of the sides of the water-permeable material and the indicator is on the other one of the sides of the sheet of water-permeable material.

14. A hydration sensor as recited in claim 8,
wherein the indicator includes a plurality of identifiers, with each identifier spaced from the aperture by a different amount,
wherein at least one of the two sheets of the water-impermeable material is substantially transparent at least in the area of the indicator,
wherein the chemical compound is a powder,
wherein the change includes forming a color patch on the water-permeable material at least due to the chemical compound on contact with saliva,
wherein the color patch is observable at least via the sheet of water-permeable material with a substantially transparent area, and
wherein the hydration level of the user depends on the identifier furthest away from the aperture that the color patch reaches, if the at least a portion of the at least one aperture is placed in contact with the saliva of the user for a predetermined duration of time, as measured by the digital timing device.

15. A hydration sensor as recited in claim 8 further comprising a handle, with the sensing element to be at an end of the handle.

* * * * *